United States Patent
Frye et al.

(10) Patent No.: US 10,906,983 B2
(45) Date of Patent: Feb. 2, 2021

(54) ANTI-CD137 ANTIBODIES

(71) Applicant: Eli Lilly and Company, Indianapolis, IN (US)

(72) Inventors: Christopher Carl Frye, Bargersville, IN (US); Michael Dewain Kalos, Brooklyn, NY (US); Helen Kotanides, Norwalk, CT (US); Stephanie Lynn Sandefur, Indianapolis, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 0 days.

(21) Appl. No.: 16/497,493

(22) PCT Filed: Jul. 25, 2018

(86) PCT No.: PCT/US2018/043632
§ 371 (c)(1),
(2) Date: Sep. 25, 2019

(87) PCT Pub. No.: WO2019/027754
PCT Pub. Date: Feb. 7, 2019

(65) Prior Publication Data
US 2020/0377607 A1    Dec. 3, 2020

Related U.S. Application Data

(60) Provisional application No. 62/539,687, filed on Aug. 1, 2017.

(51) Int. Cl.
| | | |
|---|---|---|
| *C07K 16/28* | (2006.01) | |
| *C12N 15/13* | (2006.01) | |
| *C12N 5/10* | (2006.01) | |
| *A61P 35/00* | (2006.01) | |
| *A61K 39/00* | (2006.01) | |

(52) U.S. Cl.
CPC .......... *C07K 16/2878* (2013.01); *A61P 35/00* (2018.01); *A61K 2039/505* (2013.01); *C07K 2317/56* (2013.01); *C07K 2317/75* (2013.01)

(58) Field of Classification Search
None
See application file for complete search history.

(56) References Cited

U.S. PATENT DOCUMENTS

| 7,288,638 B2 | 10/2007 | Jure-Kunkel et al. |
| 8,337,850 B2 | 12/2012 | Ahrens et al. |
| 10,689,454 B2 * | 6/2020 | Ellmark .................. A61P 35/02 |
| 2016/0244528 A1 | 8/2016 | Gray et al. |

FOREIGN PATENT DOCUMENTS

WO    2003/049755 A1    6/2003

OTHER PUBLICATIONS

Li et al., Limited cross-linking of 4-1BB by 4-1BB ligand and the agonist monoclonal antibody utomilumab, Cell Reports, 25:909-920, Oct. 23, 2018.*
Deutscher, M. P. "[8] Maintaining protein stability." Methods in enzymology. vol. 182. Academic Press, 1990. 83-89.
Emsley, P., et al. "Features and development of Coot." Acta Crystallographica Section D: Biological Crystallography 66.4 (2010): 486-501.
McCoy, A. J., et al. "Phaser crystallographic software." Journal of applied crystallography 40.4 (2007): 658-674.
Melero, I., et al. "Monoclonal antibodies against the 4-1BB T-cell activation molecule eradicate established tumors." Nature medicine 3.6 (1997): 682.
Murshudov, G. N., et al. "REFMAC5 for the refinement of macromolecular crystal structures." Acta Crystallographica Section D: Biological Crystallography 67.4 (2011): 355-367.
North, B. et al., "A New Clustering of Antibody CDR Loop Conformations", Journal of Molecular Biology, 406, 228-256 (2011).
Segal, N. H., et al. "Results from an integrated safety analysis of urelumab, an agonist anti-CD137 monoclonal antibody." Clinical Cancer Research 23.8 (2017): 1929-1936.
Winn, M. D., et al. "Overview of the CCP4 suite and current developments." Acta Crystallographica Section D: Biological Crystallography 67.4 (2011): 235-242.
Fisher, Timothy S. et al., "Targeting of 4-1BB by monoclonal antibody PF-05082566 enhances T-cell function and promotes anti-tumor activity," *Cancer Immunology Immunotherapy* 61(10): 1721-1733 (2012).
Guo, Zhiqiang et al., "Combined TIM-3 blockade and CD137 activation affords the long-term protection in a murine model of ovarian cancer." *Journal of Translational Medicine* 11(1): 215, 11 pages (2013).
International Search Report for PCT/US2018/043632 (dated Oct. 25, 2018).
Written Opinion for PCT/US2018/043632 (dated Oct. 25, 2018).

* cited by examiner

*Primary Examiner* — Claire Kaufman
(74) *Attorney, Agent, or Firm* — Quarles & Brady LLP

(57) ABSTRACT

The present invention relates to antibodies that bind to human CD137 and display agonist activity, and is useful for treating solid and hematological tumors alone and in combination with chemotherapy and ionizing radiation.

9 Claims, No Drawings

Specification includes a Sequence Listing.

ANTI-CD137 ANTIBODIES

The present invention is in the field of medicine. Particularly, the present invention relates to agonistic antibodies directed to human CD137, compositions comprising such agonistic anti-human CD137 antibodies, and methods of using such agonistic anti-human CD137 antibodies for the treatment of solid and hematological tumors alone or in combination with chemotherapy and other cancer therapeutics.

It is now known that boosting the anti-tumor immune response can be an effective means of cancer therapy. In this regard, CD137, also known as 4-1BB, belongs to the TNF receptor family and plays a role in the activation of T cell immune responses such as by driving T cell proliferation and effector functions, promoting immunological memory, and inhibiting activation-induced cell death. Agonistic antibodies targeting CD137 have shown promise in murine tumor models as a monotherapy (Melero. I. et al., *Nat. Med.* 3(6):682-685 (1997)), however, agonist antibodies targeting human CD137 have not yet demonstrated sufficient responses as a monotherapy or combination therapy in human patients. In this regard, neither utomilumab (a fully human CD137 agonist IgG2 mAb) (Fisher, T. M. et al, *Cancer Immunol. Immunother*. (2012) 61:1721-1733) nor urelumab (a humanized CD137 agonist IgG4 mAb) (Segal, N. H. *Clin. Cancer Res.* (2017) 23(8):1929-1936) have received regulatory approvals for use as a monotherapy or even as a combination therapy. Indeed, no agonistic antibody targeting human CD137 has been approved for therapeutic use in humans.

Thus, there exists a need for additional fully human antibodies that agonize the human CD137 receptor and promote a robust anti-cancer immune response, but with acceptable toxiciticy profiles. There also remains a need for alternative anti-human agonistic CD137 antibodies that can be combined with other therapeutics for the treatment of cancer. In particular, there also remains a need for anti-human CD137 antibodies that display sufficient potency as a cancer monotherapy and/or combination therapy.

Without being limited to theory, it is believed that the use of current agonistic antibodies targeting CD137 as a cancer monotherapy and/or combination agent is hampered by factors such as the agonistic strength of said antibodies and the immune-related adverse events that result from their use at higher, potentially efficacious doses. In particular, current antibodies are either too potent, leading to adverse events, or display sub-optimal efficacy.

The anti-human CD137 agonistic antibodies described herein are fully human, Fcγ-receptor-mediated effector null antibodies that bind human CD137 and cynomolgus monkey CD137, stimulate T cell activation in vitro, promote human CD137 cell surface expression, enhance NF-kappa B activity, inhibit tumor growth in murine tumor models of non-small cell lung cancer as a monotherapy, inhibit T-regulatory cell mediated suppression in vitro, activate immune gene signatures, increase the frequency of intratumoral $CD3^+$ T cells, compete with human CD137-Ligand for binding to human CD137, and bind to unique amino acid residues on human CD137.

The present disclosure provides an anti-human CD137 (SEQ ID NO:1) antibody comprising HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO:6, and LCDR3 having the amino acid sequence of SEQ ID NO: 7.

The present disclosure provides an antibody comprising a heavy chain variable region having the amino acid sequence of SEQ ID NO: 8 and a light chain variable region having the amino acid sequence of SEQ ID NO: 9. The present disclosure provides an antibody comprising a heavy chain variable region having the amino acid sequence of SEQ ID NO: 8 and a light chain variable region having the amino acid sequence of SEQ ID NO: 12.

The present disclosure provides an antibody comprising a heavy chain having the amino acid sequence of SEQ ID NO: 10 and a light chain having the amino acid sequence of SEQ ID NO: 11. The present disclosure provides an antibody comprising a heavy chain having the amino acid sequence of SEQ ID NO: 10 and a light chain having the amino acid sequence of SEQ ID NO: 13.

The present disclosure provides a mammalian cell capable of expressing an antibody comprising HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO:7.

The present disclosure provides a mammalian cell capable of expressing an antibody comprising a heavy chain having the amino acid sequence of SEQ ID NO: 10 and a light chain having the amino acid sequence of SEQ ID NO: 11 or the amino acid sequence of SEQ ID NO: 13.

The present disclosure provides a process for producing an antibody comprising cultivating a mammalian cell capable of expressing the antibody and recovering the antibody; wherein the antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7.

The present disclosure provides a process for producing an antibody comprising cultivating a mammalian cell capable of expressing the antibody and recovering the antibody; wherein the antibody comprises a heavy chain having the amino acid sequence of SEQ ID NO: 10 and a light chain having the amino acid sequence of SEQ ID NO: 11 or the amino acid sequence of SEQ ID NO: 13.

The present disclosure provides an antibody produced by a process comprising cultivating a mammalian cell capable of expressing the antibody and recovering the antibody; wherein the antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7. The present disclosure provides an antibody produced by a process comprising cultivating a mammalian cell capable of expressing the antibody and recovering the antibody; wherein the antibody comprises a heavy chain having the amino acid sequence of SEQ ID NO: 10 and a light chain having the amino acid sequence of SEQ ID NO: 11 or the amino acid sequence of SEQ ID NO: 13.

The present disclosure provides a DNA molecule comprising a polynucleotide having the sequence of SEQ ID NO:14 and one of SEQ ID NO:15, SEQ ID NO:16, or SEQ ID NO:17. The present disclosure provides a DNA molecule comprising a polynucleotide having the sequence of SEQ ID NO:14, SEQ ID NO:15, SEQ ID NO:16, or SEQ ID NO:17. The present disclosure provides a mammalian cell comprising a DNA molecule comprising a polynucleotide having the sequence of SEQ ID NO:14 and one of SEQ ID NO:15, SEQ ID NO:16, or SEQ ID NO:17. The present disclosure provides a mammalian cell comprising a DNA molecule comprising a polynucleotide having the sequence of SEQ ID NO:14, SEQ ID NO:15, SEQ ID NO:16, or SEQ ID NO:17.

The present disclosure provides a pharmaceutical composition comprising an antibody disclosed herein and an acceptable carrier, diluent, or excipient. The present disclosure provides a pharmaceutical composition comprising an antibody and an acceptable carrier, diluent, or excipient; wherein the antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO:6, and LCDR3 having the amino acid sequence of SEQ ID NO: 7. The present disclosure provides a pharmaceutical composition comprising an antibody and an acceptable carrier, diluent, or excipient; wherein the antibody comprises a heavy chain variable region having the amino acid sequence of SEQ ID NO: 8 and a light chain variable region having the amino acid sequence of SEQ ID NO: 9. The present disclosure provides a pharmaceutical composition comprising an antibody and an acceptable carrier, diluent, or excipient; wherein the antibody comprises a heavy chain variable region having the amino acid sequence of SEQ ID NO: 8 and a light chain variable region having the amino acid sequence of SEQ ID NO: 12. The present disclosure provides a pharmaceutical composition comprising an antibody and an acceptable carrier, diluent, or excipient; wherein the antibody comprises a heavy chain having the amino acid sequence of SEQ ID NO: 10 and a light chain having the amino acid sequence of SEQ ID NO: 11. The present disclosure provides a pharmaceutical composition comprising an antibody and an acceptable carrier, diluent, or excipient; wherein the antibody comprises a heavy chain having the amino acid sequence of SEQ ID NO: 10 and a light chain having the amino acid sequence of SEQ ID NO: 13.

The present disclosure provides a method of treating cancer, comprising administering to a patient in need thereof, an effective amount of an anti-human CD137 (SEQ ID NO:1) antibody comprising HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO:6, and LCDR3 having the amino acid sequence of SEQ ID NO: 7. The present disclosure provides a method of treating cancer, comprising administering to a patient in need thereof, an effective amount of an antibody comprising a heavy chain variable region having the amino acid sequence of SEQ ID NO: 8 and a light chain variable region having the amino acid sequence of SEQ ID NO: 9. The present disclosure provides a method of treating cancer, comprising administering to a patient in need thereof, an effective amount of an antibody comprising a heavy chain variable region having the amino acid sequence of SEQ ID NO: 8 and a light chain variable region having the amino acid sequence of SEQ ID NO: 12. The present disclosure provides a method of treating cancer, comprising administering to a patient in need thereof, an effective amount of an antibody comprising a heavy chain having the amino acid sequence of SEQ ID NO: 10 and a light chain having the amino acid sequence of SEQ ID NO: 11. The present disclosure provides a method of treating cancer, comprising administering to a patient in need thereof, an effective amount of an antibody comprising a heavy chain having the amino acid sequence of SEQ ID NO: 10 and a light chain having the amino acid sequence of SEQ ID NO: 13.

The present disclosure provides a method of treating cancer, comprising administering to a patient in need thereof, an effective amount of an anti-human CD137 (SEQ ID NO:1) antibody comprising HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO:6, and LCDR3 having the amino acid sequence of SEQ ID NO: 7; wherein the cancer is bladder cancer, breast cancer, biliary tract cancer, colon cancer, endometrial cancer, esophageal cancer, gastric cancer, head and neck cancer, non-small cell lung cancer, prostate cancer, rectal cancer, or thyroid cancer. The present disclosure provides a method of treating cancer, comprising administering to a patient in need thereof, an effective amount of an antibody comprising a heavy chain variable region having the amino acid sequence of SEQ ID NO: 8 and a light chain variable region having the amino acid sequence of SEQ ID NO: 9; wherein the cancer is bladder cancer, breast cancer, biliary tract cancer, colon cancer, endometrial cancer, esophageal cancer, gastric cancer, head and neck cancer, non-small cell lung cancer, prostate cancer, rectal cancer, or thyroid cancer. The present disclosure provides a method of treating cancer, comprising administering to a patient in need thereof, an effective amount of an antibody comprising a heavy chain variable region having the amino acid sequence of SEQ ID NO: 8 and a light chain variable region having the amino acid sequence of SEQ ID NO: 12; wherein the cancer is bladder cancer, breast cancer, biliary tract cancer, colon cancer, endometrial cancer, esophageal cancer, gastric cancer, head and neck cancer, non-small cell lung cancer, prostate cancer, rectal cancer, or thyroid cancer. The present disclosure provides a method of treating cancer, comprising administering to a patient in need thereof, an effective amount of an antibody comprising a heavy chain having the amino acid sequence of SEQ ID NO: 10 and a light chain having the amino acid sequence of SEQ ID NO: 11; wherein the cancer is bladder cancer, breast cancer, biliary tract cancer, colon cancer, endometrial cancer, esophageal cancer, gastric cancer, head and neck cancer, non-small cell lung cancer, prostate cancer, rectal cancer, or thyroid cancer. The present disclosure provides a method of treating cancer, comprising administering to a patient in need thereof, an effective amount of an antibody comprising a heavy chain having the amino acid sequence of SEQ ID NO: 10 and a light chain having the amino acid sequence of SEQ ID NO: 13; wherein the cancer is bladder cancer, breast cancer, biliary tract cancer, colon cancer, endometrial cancer, esophageal cancer, gastric cancer, head and neck cancer, non-small cell lung cancer, prostate cancer, rectal cancer, or thyroid cancer.

The present disclosure provides a method of treating cancer, comprising administering to a patient in need thereof, an effective amount of an anti-human CD137 (SEQ ID NO:1) antibody comprising HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO:6, and LCDR3 having the amino acid sequence of SEQ ID NO: 7; wherein the cancer is cholangiocarcinoma, head and neck squamous cell carcinoma, lung adenocarcinoma, lung squamous cell carcinoma, clear cell renal carcinoma, or head and neck squamous cell carcinoma.

The present disclosure provides a method of treating cancer, comprising administering to a patient in need thereof, an effective amount of an antibody comprising a heavy chain variable region having the amino acid sequence of SEQ ID NO: 8 and a light chain variable region having the amino acid sequence of SEQ ID NO: 9; wherein the cancer is cholangiocarcinoma, head and neck squamous cell carcinoma, lung adenocarcinoma, lung squamous cell carcinoma, clear cell renal carcinoma, or head and neck squamous cell carcinoma. The present disclosure provides a method of treating cancer, comprising administering to a patient in need thereof, an effective amount of an antibody comprising a heavy chain variable region having the amino acid sequence of SEQ ID NO: 8 and a light chain variable region having the amino acid sequence of SEQ ID NO: 12; wherein the cancer is cholangiocarcinoma, head and neck squamous cell carcinoma, lung adenocarcinoma, lung squamous cell carcinoma, clear cell renal carcinoma, or head and neck squamous cell carcinoma. The present disclosure provides a method of treating cancer, comprising administering to a patient in need thereof, an effective amount of an antibody comprising a heavy chain having the amino acid sequence of SEQ ID NO: 10 and a light chain having the amino acid sequence of SEQ ID NO: 11; wherein the cancer is cholangiocarcinoma, head and neck squamous cell carcinoma, lung adenocarcinoma, lung squamous cell carcinoma, clear cell renal carcinoma, or head and neck squamous cell carcinoma. The present disclosure provides a method of treating cancer, comprising administering to a patient in need thereof, an effective amount of an antibody comprising a heavy chain having the amino acid sequence of SEQ ID NO: 10 and a light chain having the amino acid sequence of SEQ ID NO: 13; wherein the cancer is cholangiocarcinoma, head and neck squamous cell carcinoma, lung adenocarcinoma, lung squamous cell carcinoma, clear cell renal carcinoma, or head and neck squamous cell carcinoma.

The present disclosure provides a method of treating cancer, comprising administering to a patient in need thereof, an effective amount of an anti-human CD137 (SEQ ID NO:1) antibody comprising HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO:6, and LCDR3 having the amino acid sequence of SEQ ID NO: 7; wherein the antibody is administered in simultaneous, separate, or sequential combination with ionizing radiation. The present disclosure provides a method of treating cancer, comprising administering to a patient in need thereof, an effective amount of an antibody comprising a heavy chain variable region having the amino acid sequence of SEQ ID NO: 8 and a light chain variable region having the amino acid sequence of SEQ ID NO: 9; wherein the antibody is administered in simultaneous, separate, or sequential combination with ionizing radiation. The present disclosure provides a method of treating cancer, comprising administering to a patient in need thereof, an effective amount of an antibody comprising a heavy chain variable region having the amino acid sequence of SEQ ID NO: 8 and a light chain variable region having the amino acid sequence of SEQ ID NO: 12; wherein the antibody is administered in simultaneous, separate, or sequential combination with ionizing radiation. The present disclosure provides a method of treating cancer, comprising administering to a patient in need thereof, an effective amount of an antibody comprising a heavy chain having the amino acid sequence of SEQ ID NO: 10 and a light chain having the amino acid sequence of SEQ ID NO: 11; wherein the antibody is administered in simultaneous, separate, or sequential combination with ionizing radiation. The present disclosure provides a method of treating cancer, comprising administering to a patient in need thereof, an effective amount of an antibody comprising a heavy chain having the amino acid sequence of SEQ ID NO: 10 and a light chain having the amino acid sequence of SEQ ID NO: 13; wherein the antibody is administered in simultaneous, separate, or sequential combination with ionizing radiation.

The present disclosure provides a method of treating cancer, comprising administering to a patient in need thereof, an effective amount of an anti-human CD137 (SEQ ID NO:1) antibody comprising HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO:6, and LCDR3 having the amino acid sequence of SEQ ID NO: 7; wherein the antibody is administered in simultaneous, separate, or sequential combination with one or more chemotherapeutic agents. The present disclosure provides a method of treating cancer, comprising administering to a patient in need thereof, an effective amount of an antibody comprising a heavy chain variable region having the amino acid sequence of SEQ ID NO: 8 and a light chain variable region having the amino acid sequence of SEQ ID NO: 9; wherein the antibody is administered in simultaneous, separate, or sequential combination with one or more chemotherapeutic agents. The present disclosure provides a method of treating cancer, comprising administering to a patient in need thereof, an effective amount of an antibody comprising a heavy chain variable region having the amino acid sequence of SEQ ID NO: 8 and a light chain variable region having the amino acid sequence of SEQ ID NO: 12; wherein the antibody is administered in simultaneous, separate, or sequential combination with one or more chemotherapeutic agents. The present disclosure provides a method of treating cancer, comprising administering to a patient in need thereof, an effective amount of an antibody comprising a heavy chain having the amino acid sequence of SEQ ID NO: 10 and a light chain having the amino acid sequence of SEQ ID NO: 11; wherein the antibody is administered in simultaneous, separate, or sequential combination with one or more chemotherapeutic agents. The present disclosure provides a method of treating cancer, comprising administering to a patient in need thereof, an effective amount of an antibody comprising a heavy chain having the amino acid sequence of SEQ ID NO: 10 and a light chain having the amino acid sequence of SEQ ID NO: 13; wherein the antibody is administered in simultaneous, separate, or sequential combination with one or more chemotherapeutic agents.

The present disclosure provides an antibody disclosed herein for use in the treatment of cancer; wherein the cancer is bladder cancer. The present disclosure provides an antibody disclosed herein for use in the treatment of cancer; wherein the cancer is breast cancer. The present disclosure provides an antibody disclosed herein for use in the treatment of cancer; wherein the cancer is biliary tract cancer. The present disclosure provides an antibody disclosed herein for use in the treatment of cancer; wherein the cancer is colon cancer. The present disclosure provides an antibody disclosed herein for use in the treatment of cancer; wherein the cancer is endometrial cancer. The present disclosure provides an antibody disclosed herein for use in the treatment of cancer; wherein the cancer is esophageal cancer. The present disclosure provides an antibody disclosed herein for use in the treatment of cancer; wherein the cancer is gastric cancer. The present disclosure provides an antibody disclosed herein for use in the treatment of cancer; wherein the cancer is head and neck cancer. The present disclosure provides an antibody disclosed herein for use in the treatment of cancer; wherein the cancer is non-small cell lung cancer. The present disclosure provides an antibody disclosed herein for use in the treatment of cancer; wherein the cancer is prostate cancer. The present disclosure provides an antibody disclosed herein for use in the treatment of cancer; wherein the cancer is rectal cancer. The present disclosure provides an antibody disclosed herein for use in the treatment of cancer; wherein the cancer is thyroid cancer. The present disclosure provides an antibody disclosed herein for use in the treatment of cancer; wherein the cancer is head and neck squamous cell carcinoma. The present disclosure provides an antibody disclosed herein for use in the treatment of cancer; wherein the cancer is renal cell carcinoma. The present disclosure provides an antibody disclosed herein for use in the treatment of cancer; wherein the cancer is cholangiocarcinoma. The present disclosure provides an antibody disclosed herein for use in the treatment of cancer; wherein the cancer is lung adenocarcinoma. The present disclosure provides an antibody disclosed herein for use in the treatment of cancer; wherein the cancer is lung squamous cell carcinoma. The present disclosure provides an antibody disclosed herein for use in the treatment of cancer; wherein the cancer is clear cell renal carcinoma.

The present disclosure provides the use of an antibody disclosed herein for the manufacture of a medicament for the treatment of cancer; wherein the cancer is bladder cancer. The present disclosure provides the use of an antibody disclosed herein for the manufacture of a medicament for the treatment of cancer; wherein the cancer is breast cancer. The present disclosure provides the use of an antibody disclosed herein for the manufacture of a medicament for the treatment of cancer; wherein the cancer is biliary tract cancer. The present disclosure provides the use of an antibody disclosed herein for the manufacture of a medicament for the treatment of cancer; wherein the cancer is colon cancer. The present disclosure provides the use of an antibody disclosed herein for the manufacture of a medicament for the treatment of cancer; wherein the cancer is endometrial cancer. The present disclosure provides the use of an antibody disclosed herein for the manufacture of a medicament for the treatment of cancer; wherein the cancer is esophageal cancer. The present disclosure provides the use of an antibody disclosed herein for the manufacture of a medicament for the treatment of cancer; wherein the cancer is gastric cancer. The present disclosure provides the use of an antibody disclosed herein for the manufacture of a medicament for the treatment of cancer; wherein the cancer is head and neck cancer. The present disclosure provides the use of an antibody disclosed herein for the manufacture of a medicament for the treatment of cancer; wherein the cancer is non-small cell lung cancer. The present disclosure provides the use of an antibody disclosed herein for the manufacture of a medicament for the treatment of cancer; wherein the cancer is prostate cancer. The present disclosure provides the use of an antibody disclosed herein for the manufacture of a medicament for the treatment of cancer; wherein the cancer is rectal cancer. The present disclosure provides the use of an antibody disclosed herein for the manufacture of a medicament for the treatment of cancer; wherein the cancer is thyroid cancer. The present disclosure provides the use of an antibody disclosed herein for the manufacture of a medicament for the treatment of cancer; wherein the cancer is head and neck squamous cell carcinoma. The present disclosure provides the use of an antibody disclosed herein for the manufacture of a medicament for the treatment of cancer; wherein the cancer is renal cell carcinoma. The present disclosure provides the use of an antibody disclosed herein for the manufacture of a medicament for the treatment of cancer; wherein the cancer is cholangiocarcinoma. The present disclosure provides the use of an antibody disclosed herein for the manufacture of a medicament for the treatment of cancer; wherein the cancer is lung adenocarcinoma. The present disclosure provides the use of an antibody disclosed herein for the manufacture of a medicament for the treatment of cancer; wherein the cancer is lung squamous cell carcinoma. The present disclosure provides the use of an antibody disclosed herein for the manufacture of a medicament for the treatment of cancer; wherein the cancer is clear cell renal carcinoma.

The present disclosure provides an anti-human CD137 (SEQ ID NO:1) antibody disclosed herein for use in therapy. The present disclosure provides an anti-human CD137 (SEQ ID NO:1) antibody disclosed herein for use in therapy; wherein the antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO:6, and LCDR3 having the amino acid sequence of SEQ ID NO: 7. The present disclosure provides an anti-human CD137 (SEQ ID NO:1) antibody disclosed herein for use in therapy; wherein the antibody comprises a heavy chain having the amino acid sequence of SEQ ID NO: 10 and a light chain having the amino acid sequence of SEQ ID NO: 11. The present disclosure provides an anti-human CD137 (SEQ ID NO:1) antibody disclosed herein for use in therapy; wherein the antibody comprises a heavy chain having the amino acid sequence of SEQ ID NO: 10 and a light chain having the amino acid sequence of SEQ ID NO: 13.

The present disclosure provides an anti-human CD137 (SEQ ID NO:1) antibody for use in the treatment of cancer, wherein the antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO:6, and LCDR3 having the amino acid sequence of SEQ ID NO: 7. The present disclosure provides an antibody for use in the treatment of cancer, wherein the antibody comprises a heavy chain variable region having the amino acid sequence of SEQ ID NO: 8 and a light chain variable region having the amino acid sequence of SEQ ID NO: 9. The present disclosure provides an antibody for use in the treatment of cancer, wherein the antibody comprises a heavy chain variable region having the amino acid sequence of SEQ ID NO: 8 and a light chain variable region having the amino acid sequence of SEQ ID NO: 12. The present disclosure provides an antibody for use in the treatment of cancer, wherein the antibody comprises a heavy chain having the amino acid sequence of SEQ ID NO: 10 and a light chain having the amino acid sequence of SEQ ID NO: 11. The present disclosure provides an antibody for use in the treatment of cancer, wherein the antibody comprises a heavy chain having the amino acid sequence of SEQ ID NO: 10 and a light chain having the amino acid sequence of SEQ ID NO: 13.

The present disclosure provides an anti-human CD137 (SEQ ID NO:1) antibody for use in the treatment of cancer, wherein the antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO:6, and LCDR3 having the amino acid sequence of SEQ ID NO: 7; wherein the cancer is bladder cancer, breast cancer, biliary tract cancer, colon cancer, endometrial cancer, esophageal cancer, gastric cancer, head and neck cancer, non-small cell lung cancer, prostate cancer, rectal cancer, or thyroid cancer. The present disclosure provides an antibody for use in the treatment of cancer, wherein the antibody comprises a heavy chain variable region having the amino acid sequence of SEQ ID NO: 8 and a light chain variable region having the amino acid sequence of SEQ ID NO: 9; wherein the cancer is bladder cancer, breast cancer, biliary tract cancer, colon cancer, endometrial cancer, esophageal cancer, gastric cancer, head and neck cancer, non-small cell lung cancer, prostate cancer, rectal cancer, or thyroid cancer. The present disclosure provides an antibody for use in the treatment of cancer, wherein the antibody comprises a heavy chain variable region having the amino acid sequence of SEQ ID NO: 8 and a light chain variable region having the amino acid sequence of SEQ ID NO: 12; wherein the cancer is bladder cancer, breast cancer, biliary tract cancer, colon cancer, endometrial cancer, esophageal cancer, gastric cancer, head and neck cancer, non-small cell lung cancer, prostate cancer, rectal cancer, or thyroid cancer. The present disclosure provides an antibody for use in the treatment of cancer, wherein the antibody comprises a heavy chain having the amino acid sequence of SEQ ID NO: 10 and a light chain having the amino acid sequence of SEQ ID NO: 11; wherein the cancer is bladder cancer, breast cancer, biliary tract cancer, colon cancer, endometrial cancer, esophageal cancer, gastric cancer, head and neck cancer, non-small cell lung cancer, prostate cancer, rectal cancer, or thyroid cancer. The present disclosure provides an antibody for use in the treatment of cancer, wherein the antibody comprises a heavy chain having the amino acid sequence of SEQ ID NO: 10 and a light chain having the amino acid sequence of SEQ ID NO: 13; wherein the cancer is bladder cancer, breast cancer, biliary tract cancer, colon cancer, endometrial cancer, esophageal cancer, gastric cancer, head and neck cancer, non-small cell lung cancer, prostate cancer, rectal cancer, or thyroid cancer.

The present disclosure provides an anti-human CD137 (SEQ ID NO:1) antibody for use in the treatment of cancer, wherein the antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO:6, and LCDR3 having the amino acid sequence of SEQ ID NO: 7; wherein the cancer is cholangiocarcinoma, head and neck squamous cell carcinoma, lung adenocarcinoma, lung squamous cell carcinoma, clear cell renal carcinoma, or head and neck squamous cell carcinoma. The present disclosure provides an antibody for use in the treatment of cancer, wherein the antibody comprises a heavy chain variable region having the amino acid sequence of SEQ ID NO: 8 and a light chain variable region having the amino acid sequence of SEQ ID NO: 9; wherein the cancer is cholangiocarcinoma, head and neck squamous cell carcinoma, lung adenocarcinoma, lung squamous cell carcinoma, clear cell renal carcinoma, or head and neck squamous cell carcinoma. The present disclosure provides an antibody for use in the treatment of cancer, wherein the antibody comprises a heavy chain variable region having the amino acid sequence of SEQ ID NO: 8 and a light chain variable region having the amino acid sequence of SEQ ID NO: 12; wherein the cancer is cholangiocarcinoma, head and neck squamous cell carcinoma, lung adenocarcinoma, lung squamous cell carcinoma, clear cell renal carcinoma, or head and neck squamous cell carcinoma. The present disclosure provides an antibody for use in the treatment of cancer, wherein the antibody comprises a heavy chain having the amino acid sequence of SEQ ID NO: 10 and a light chain having the amino acid sequence of SEQ ID NO: 11; wherein the cancer is cholangiocarcinoma, head and neck squamous cell carcinoma, lung adenocarcinoma, lung squamous cell carcinoma, clear cell renal carcinoma, or head and neck squamous cell carcinoma. The present disclosure provides an antibody for use in the treatment of cancer, wherein the antibody comprises a heavy chain having the amino acid sequence of SEQ ID NO: 10 and a light chain having the amino acid sequence of SEQ ID NO: 13; wherein the cancer is cholangiocarcinoma, head and neck squamous cell carcinoma, lung adenocarcinoma, lung squamous cell carcinoma, clear cell renal carcinoma, or head and neck squamous cell carcinoma.

The present disclosure provides an anti-human CD137 (SEQ ID NO:1) antibody for use in the treatment of cancer, wherein the antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO:6, and LCDR3 having the amino acid sequence of SEQ ID NO: 7; wherein the antibody is administered in simultaneous, separate, or sequential combination with ionizing radiation. The present disclosure provides an antibody for use in the treatment of cancer, wherein the antibody comprises a heavy chain variable region having the amino acid sequence of SEQ ID NO: 8 and a light chain variable region having the amino acid sequence of SEQ ID NO: 9; wherein the antibody is administered in simultaneous, separate, or sequential combination with ionizing radiation. The present disclosure provides an antibody for use in the treatment of cancer, wherein the antibody comprises a heavy chain variable region having the amino acid sequence of SEQ ID NO: 8 and a light chain variable region having the amino acid sequence of SEQ ID NO: 12; wherein the antibody is administered in simultaneous, separate, or sequential combination with ionizing radiation. The present disclosure provides an antibody for use in the treatment of cancer, wherein the antibody comprises a heavy chain having the amino acid sequence of SEQ ID NO: 10 and a light chain having the amino acid sequence of SEQ ID NO: 11; wherein the antibody is administered in simultaneous, separate, or sequential combination with ionizing radiation. The present disclosure provides an antibody for use in the treatment of cancer, wherein the antibody comprises a heavy chain having the amino acid sequence of SEQ ID NO: 10 and a light chain having the amino acid sequence of SEQ ID NO: 13; wherein the antibody is administered in simultaneous, separate, or sequential combination with ionizing radiation.

The present disclosure provides an anti-human CD137 (SEQ ID NO:1) antibody for use in the treatment of cancer, wherein the antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO:6, and LCDR3 having the amino acid sequence of SEQ ID NO: 7; wherein the antibody is administered in simultaneous, separate, or sequential combination with one or more chemotherapeutic agents. The present disclosure provides an antibody for use in the treatment of cancer, wherein the antibody comprises a heavy chain variable region having the amino acid sequence of SEQ ID NO: 8 and a light chain variable region having the amino acid sequence of SEQ ID NO: 9; wherein the antibody is administered in simultaneous, separate, or sequential combination with one or more chemotherapeutic agents. The present disclosure provides an antibody for use in the treatment of cancer, wherein the antibody comprises a heavy chain variable region having the amino acid sequence of SEQ ID NO: 8 and a light chain variable region having the amino acid sequence of SEQ ID NO: 12; wherein the antibody is administered in simultaneous, separate, or sequential combination with one or more chemotherapeutic agents. The present disclosure provides an antibody for use in the treatment of cancer, wherein the antibody comprises a heavy chain having the amino acid sequence of SEQ ID NO: 10 and a light chain having the amino acid sequence of SEQ ID NO: 11; wherein the antibody is administered in simultaneous, separate, or sequential combination with one or more chemotherapeutic agents. The present disclosure provides an antibody for use in the treatment of cancer, wherein the antibody comprises a heavy chain having the amino acid sequence of SEQ ID NO: 10 and a light chain having the amino acid sequence of SEQ ID NO: 13; wherein the antibody is administered in simultaneous, separate, or sequential combination with one or more chemotherapeutic agents.

The present disclosure provides the use of an anti-human CD137 (SEQ ID NO:1) antibody for the manufacture of a medicament for the treatment of cancer, wherein the antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO:6, and LCDR3 having the amino acid sequence of SEQ ID NO: 7. The present disclosure provides the use of an antibody for the manufacture of a medicament for the treatment of cancer, wherein the antibody comprises a heavy chain variable region having the amino acid sequence of SEQ ID NO: 8 and a light chain variable region having the amino acid sequence of SEQ ID NO: 9. The present disclosure provides the use of an antibody for the manufacture of a medicament for the treatment of cancer, wherein the antibody comprises a heavy chain variable region having the amino acid sequence of SEQ ID NO: 8 and a light chain variable region having the amino acid sequence of SEQ ID NO: 12. The present disclosure provides the use of an antibody for the manufacture of a medicament for the treatment of cancer, wherein the antibody comprises a heavy chain having the amino acid sequence of SEQ ID NO: 10 and a light chain having the amino acid sequence of SEQ ID NO: 11. The present disclosure provides the use of an antibody for the manufacture of a medicament for the treatment of cancer, wherein the antibody comprises a heavy chain having the amino acid sequence of SEQ ID NO: 10 and a light chain having the amino acid sequence of SEQ ID NO: 13.

The present disclosure provides the use of an anti-human CD137 (SEQ ID NO:1) antibody for the manufacture of a medicament for the treatment of cancer, wherein the antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO:6, and LCDR3 having the amino acid sequence of SEQ ID NO: 7; wherein the cancer is bladder cancer, breast cancer, biliary tract cancer, colon cancer, endometrial cancer, esophageal cancer, gastric cancer, head and neck cancer, non-small cell lung cancer, prostate cancer, rectal cancer, or thyroid cancer. The present disclosure provides the use of an antibody for the manufacture of a medicament for the treatment of cancer, wherein the antibody comprises a heavy chain variable region having the amino acid sequence of SEQ ID NO: 8 and a light chain variable region having the amino acid sequence of SEQ ID NO: 9; wherein the cancer is bladder cancer, breast cancer, biliary tract cancer, colon cancer, endometrial cancer, esophageal cancer, gastric cancer, head and neck cancer, non-small cell lung cancer, prostate cancer, rectal cancer, or thyroid cancer. The present disclosure provides the use of an antibody for the manufacture of a medicament for the treatment of cancer, wherein the antibody comprises a heavy chain variable region having the amino acid sequence of SEQ ID NO: 8 and a light chain variable region having the amino acid sequence of SEQ ID NO: 12; wherein the cancer is bladder cancer, breast cancer, biliary tract cancer, colon cancer, endometrial cancer, esophageal cancer, gastric cancer, head and neck cancer, non-small cell lung cancer, prostate cancer, rectal cancer, or thyroid cancer. The present disclosure provides the use of an antibody for the manufacture of a medicament for the treatment of cancer, wherein the antibody comprises a heavy chain having the amino acid sequence of SEQ ID NO: 10 and a light chain having the amino acid sequence of SEQ ID NO: 11; wherein the cancer is bladder cancer, breast cancer, biliary tract cancer, colon cancer, endometrial cancer, esophageal cancer, gastric cancer, head and neck cancer, non-small cell lung cancer, prostate cancer, rectal cancer, or thyroid cancer. The present disclosure provides the use of an antibody for the manufacture of a medicament for the treatment of cancer, wherein the antibody comprises a heavy chain having the amino acid sequence of SEQ ID NO: 10 and a light chain having the amino acid sequence of SEQ ID NO: 13; wherein the cancer is bladder cancer, breast cancer, biliary tract cancer, colon cancer, endometrial cancer, esophageal cancer, gastric cancer, head and neck cancer, non-small cell lung cancer, prostate cancer, rectal cancer, or thyroid cancer.

The present disclosure provides the use of an anti-human CD137 (SEQ ID NO:1) antibody for the manufacture of a medicament for the treatment of cancer, wherein the antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO:6, and LCDR3 having the amino acid sequence of SEQ ID NO: 7; wherein the cancer is cholangiocarcinoma, head and neck squamous cell carcinoma, lung adenocarcinoma, lung squamous cell carcinoma, clear cell renal carcinoma, or head and neck squamous cell carcinoma. The present disclosure provides the use of an antibody for the manufacture of a medicament for the treatment of cancer, wherein the antibody comprises a heavy chain variable region having the amino acid sequence of SEQ ID NO: 8 and a light chain variable region having the amino acid sequence of SEQ ID NO: 9; wherein the cancer is cholangiocarcinoma, head and neck squamous cell carcinoma, lung adenocarcinoma, lung squamous cell carcinoma, clear cell renal carcinoma, or head and neck squamous cell carcinoma. The present disclosure provides the use of an antibody for the manufacture of a medicament for the treatment of cancer, wherein the antibody comprises a heavy chain variable region having the amino acid sequence of SEQ ID NO: 8 and a light chain variable region having the amino acid sequence of SEQ ID NO: 12; wherein the cancer is cholangiocarcinoma, head and neck squamous cell carcinoma, lung adenocarcinoma, lung squamous cell carcinoma, clear cell renal carcinoma, or head and neck squamous cell carcinoma. The present disclosure provides the use of an antibody for the manufacture of a medicament for the treatment of cancer, wherein the antibody comprises a heavy chain having the amino acid sequence of SEQ ID NO: 10 and a light chain having the amino acid sequence of SEQ ID NO: 11; wherein the cancer is cholangiocarcinoma, head and neck squamous cell carcinoma, lung adenocarcinoma, lung squamous cell carcinoma, clear cell renal carcinoma, or head and neck squamous cell carcinoma. The present disclosure provides the use of an antibody for the manufacture of a medicament for the treatment of cancer, wherein the antibody comprises a heavy chain having the amino acid sequence of SEQ ID NO: 10 and a light chain having the amino acid sequence of SEQ ID NO: 13; wherein the cancer is cholangiocarcinoma, head and neck squamous cell carcinoma, lung adenocarcinoma, lung squamous cell carcinoma, clear cell renal carcinoma, or head and neck squamous cell carcinoma.

The present disclosure provides the use of an anti-human CD137 (SEQ ID NO:1) antibody for the manufacture of a medicament for the treatment of cancer, wherein the antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO:6, and LCDR3 having the amino acid sequence of SEQ ID NO: 7; wherein the antibody is administered in simultaneous, separate, or sequential combination with ionizing radiation. The present disclosure provides the use of an antibody for the manufacture of a medicament for the treatment of cancer, wherein the antibody comprises a heavy chain variable region having the amino acid sequence of SEQ ID NO: 8 and a light chain variable region having the amino acid sequence of SEQ ID NO: 9; wherein the antibody is administered in simultaneous, separate, or sequential combination with ionizing radiation. The present disclosure provides the use of an antibody for the manufacture of a medicament for the treatment of cancer, wherein the antibody comprises a heavy chain variable region having the amino acid sequence of SEQ ID NO: 8 and a light chain variable region having the amino acid sequence of SEQ ID NO: 12; wherein the antibody is administered in simultaneous, separate, or sequential combination with ionizing radiation. The present disclosure provides the use of an antibody for the manufacture of a medicament for the treatment of cancer, wherein the antibody comprises a heavy chain having the amino acid sequence of SEQ ID NO: 10 and a light chain having the amino acid sequence of SEQ ID NO: 11; wherein the antibody is administered in simultaneous, separate, or sequential combination with ionizing radiation. The present disclosure provides the use of an antibody for the manufacture of a medicament for the treatment of cancer, wherein the antibody comprises a heavy chain having the amino acid sequence of SEQ ID NO: 10 and a light chain having the amino acid sequence of SEQ ID NO: 13; wherein the antibody is administered in simultaneous, separate, or sequential combination with ionizing radiation.

The present disclosure provides the use of an anti-human CD137 (SEQ ID NO:1) antibody for the manufacture of a medicament for the treatment of cancer, wherein the antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO:6, and LCDR3 having the amino acid sequence of SEQ ID NO: 7; wherein the antibody is administered in simultaneous, separate, or sequential combination with one or more chemotherapeutic agents. The present disclosure provides the use of an antibody for the manufacture of a medicament for the treatment of cancer, wherein the antibody comprises a heavy chain variable region having the amino acid sequence of SEQ ID NO: 8 and a light chain variable region having the amino acid sequence of SEQ ID NO: 9; wherein the antibody is administered in simultaneous, separate, or sequential combination with one or more chemotherapeutic agents. The present disclosure provides the use of an antibody for the manufacture of a medicament for the treatment of cancer, wherein the antibody comprises a heavy chain variable region having the amino acid sequence of SEQ ID NO: 8 and a light chain variable region having the amino acid sequence of SEQ ID NO: 12; wherein the antibody is administered in simultaneous, separate, or sequential combination with one or more chemotherapeutic agents. The present disclosure provides the use of an antibody for the manufacture of a medicament for the treatment of cancer, wherein the antibody comprises a heavy chain having the amino acid sequence of SEQ ID NO: 10 and a light chain having the amino acid sequence of SEQ ID NO: 11; wherein the antibody is administered in simultaneous, separate, or sequential combination with one or more chemotherapeutic agents. The present disclosure provides the use of an antibody for the manufacture of a medicament for the treatment of cancer, wherein the antibody comprises a heavy chain having the amino acid sequence of SEQ ID NO: 10 and a light chain having the amino acid sequence of SEQ ID NO: 13; wherein the antibody is administered in simultaneous, separate, or sequential combination with one or more chemotherapeutic agents.

The present disclosure provides an antibody that agonizes human CD137 (SEQ ID NO: 1) or a pharmaceutical composition comprising the antibody, wherein the antibody contacts human CD137 on at least one of the following amino acid residues: 55, 59, 63, 66, 72, 93-103 (inclusive); optionally, wherein the antibody contacts at least two of the residues, preferably at least three of the resides, more preferably at least four of the residues; more preferably at least five of the residues; more preferably at least six of the residues; more preferably at least seven of the residues; more preferably at least eight of the residues; more preferably at least nine of the residues; more preferably at least ten of the residues; more preferably at least eleven of the residues; more preferably at least twelve of the residues;

more preferably at least thirteen of the residues; more preferably at least fourteen of the residues; more preferably at least fifteen of the residues; or more preferably all of the residues. The present disclosure provides an antibody that agonizes human CD137 (SEQ ID NO: 1) or a pharmaceutical composition comprising the antibody, wherein the antibody contacts human CD137 on at least one of the following amino acid residues: 55, 59, 63, 66, 72, 93-103 (inclusive); optionally, wherein the antibody contacts at least two of the residues, preferably at least three of the resides, more preferably at least four of the residues; more preferably at least five of the residues; more preferably at least six of the residues; more preferably at least seven of the residues; more preferably at least eight of the residues; more preferably at least nine of the residues; more preferably at least ten of the residues; more preferably at least eleven of the residues; more preferably at least twelve of the residues; more preferably at least thirteen of the residues; more preferably at least fourteen of the residues; more preferably at least fifteen of the residues; or more preferably all of the residues; wherein contact is determined by X-ray crystallography and wherein the residues in contact are within six (6) angstroms or less of the antibody.

The present disclosure provides the use of an antibody that agonizes human CD137 (SEQ ID NO: 1) for the treatment of cancer or for the manufacture of a medicament for the treatment of cancer, wherein the antibody contacts human CD137 on at least one of the following amino acid residues: 55, 59, 63, 66, 72, 93-103 (inclusive); optionally, wherein the antibody contacts at least two of the residues, preferably at least three of the resides, more preferably at least four of the residues; more preferably at least five of the residues; more preferably at least six of the residues; more preferably at least seven of the residues; more preferably at least eight of the residues; more preferably at least nine of the residues; more preferably at least ten of the residues; more preferably at least eleven of the residues; more preferably at least twelve of the residues; more preferably at least thirteen of the residues; more preferably at least fourteen of the residues; more preferably at least fifteen of the residues; or more preferably all of the residues. The present disclosure provides the use of an antibody that agonizes human CD137 (SEQ ID NO: 1) for the treatment of cancer or for the manufacture of a medicament for the treatment of cancer, wherein the antibody contacts human CD137 on at least one of the following amino acid residues: 55, 59, 63, 66, 72, 93-103 (inclusive); optionally, wherein the antibody contacts at least two of the residues, preferably at least three of the resides, more preferably at least four of the residues; more preferably at least five of the residues; more preferably at least six of the residues; more preferably at least seven of the residues; more preferably at least eight of the residues; more preferably at least nine of the residues; more preferably at least ten of the residues; more preferably at least eleven of the residues; more preferably at least twelve of the residues; more preferably at least thirteen of the residues; more preferably at least fourteen of the residues; more preferably at least fifteen of the residues; or more preferably all of the residues; wherein contact is determined by X-ray crystallography and wherein the residues in contact are within six (6) angstroms or less of the antibody.

The present disclosure provides an antibody that agonizes human CD137 (SEQ ID NO: 1) or a pharmaceutical composition comprising the antibody, wherein the antibody contacts human CD137 at the following amino acid residues: 55, 59, 63, 66, 72, 93-103 (inclusive), and 112-116 (inclusive). The present disclosure provides an antibody that agonizes human CD137 (SEQ ID NO: 1) or a pharmaceutical composition comprising the antibody, wherein the antibody contacts human CD137 at the following amino acid residues: 55, 59, 63, 66, 72, 93-103 (inclusive), and 112-116 (inclusive); wherein contact is determined by X-ray crystallography and wherein the residues in contact are within six (6) angstroms or less of the antibody.

The present disclosure provides an antibody that agonizes human CD137 (SEQ ID NO: 1) or a pharmaceutical composition comprising the antibody, wherein the antibody contacts human CD137 at the following amino acid residues: 55, 59, 63, 66, 72, 93-103 (inclusive), and 112-116 (inclusive); wherein the cancer is bladder cancer, breast cancer, biliary tract cancer, colon cancer, endometrial cancer, esophageal cancer, gastric cancer, head and neck cancer, non-small cell lung cancer, prostate cancer, rectal cancer, or thyroid cancer. The present disclosure provides an antibody that agonizes human CD137 (SEQ ID NO: 1) or a pharmaceutical composition comprising the antibody, wherein the antibody contacts human CD137 at the following amino acid residues: 55, 59, 63, 66, 72, 93-103 (inclusive), and 112-116 (inclusive); wherein contact is determined by X-ray crystallography and wherein the residues in contact are within six (6) angstroms or less of the antibody; wherein the cancer is bladder cancer, breast cancer, biliary tract cancer, colon cancer, endometrial cancer, esophageal cancer, gastric cancer, head and neck cancer, non-small cell lung cancer, prostate cancer, rectal cancer, or thyroid cancer.

The present disclosure provides an antibody that agonizes human CD137 (SEQ ID NO: 1) for use in the treatment of cancer or for the manufacture of a medicament for the treatment of cancer, wherein the antibody contacts human CD137 at the following amino acid residues: 55, 59, 63, 66, 72, 93-103 (inclusive), and 112-116 (inclusive). The present disclosure provides an antibody that agonizes human CD137 (SEQ ID NO: 1) for use in the treatment of cancer or for the manufacture of a medicament for the treatment of cancer, wherein the antibody contacts human CD137 at the following amino acid residues: 55, 59, 63, 66, 72, 93-103 (inclusive), and 112-116 (inclusive); wherein contact is determined by X-ray crystallography and wherein the residues in contact are within six (6) angstroms or less of the antibody.

The present disclosure provides an antibody that agonizes human CD137 (SEQ ID NO: 1) for use in the treatment of cancer or the use of an antibody that agonizes human CD137 (SEQ ID NO: 1) for the manufacture of a medicament for the treatment of cancer, wherein the antibody contacts human CD137 at the following amino acid residues: 55, 59, 63, 66, 72, 93-103 (inclusive), and 112-116 (inclusive); wherein the cancer is bladder cancer, breast cancer, biliary tract cancer, colon cancer, endometrial cancer, esophageal cancer, gastric cancer, head and neck cancer, non-small cell lung cancer, prostate cancer, rectal cancer, or thyroid cancer. The present disclosure provides an antibody that agonizes human CD137 (SEQ ID NO: 1) for use in the treatment of cancer or the use of an antibody that agonizes human CD137 (SEQ ID NO: 1) for the manufacture of a medicament for the treatment of cancer, wherein the antibody contacts human CD137 at the following amino acid residues: 55, 59, 63, 66, 72, 93-103 (inclusive), and 112-116 (inclusive); wherein contact is determined by X-ray crystallography and wherein the residues in contact are within six (6) angstroms or less of the antibody; wherein the cancer is bladder cancer, breast cancer, biliary tract cancer, colon cancer, endometrial cancer, esophageal cancer, gastric cancer, head and neck cancer, non-small cell lung cancer, prostate cancer, rectal cancer, or thyroid cancer.

The present disclosure provides an antibody that agonizes human CD137 (SEQ ID NO: 1) or a pharmaceutical composition comprising the antibody, wherein the antibody does not bind human FcγRI, human FcγRIIa, human FcγRIIb, human FcγRIIIa(F), human FcγRIIIa(V), or human C1q. The present disclosure provides an antibody that agonizes human CD137 (SEQ ID NO: 1) for use in the treatment of cancer or for the manufacture of a medicament for the treatment of cancer, wherein the antibody does not bind human FcγRI, human FcγRIIa, human FcγRIIb, human FcγRIIIa(F), human FcγRIIIa(V), or human C1q.

The present disclosure provides an antibody that agonizes human CD137 (SEQ ID NO: 1) or a pharmaceutical composition comprising the antibody, wherein the antibody does not bind human FcγRI, human FcγRIIa, human FcγRIIb, human FcγRIIIa(F), human FcγRIIIa(V), or human C1 q; wherein the cancer is bladder cancer, breast cancer, biliary tract cancer, colon cancer, endometrial cancer, esophageal cancer, gastric cancer, head and neck cancer, non-small cell lung cancer, prostate cancer, rectal cancer, or thyroid cancer. The present disclosure provides an antibody that agonizes human CD137 (SEQ ID NO: 1) for use in the treatment of cancer or for the manufacture of a medicament for the treatment of cancer, wherein the antibody does not bind human FcγRI, human FcγRIIa, human FcγRIIb, human FcγRIIIa(F), human FcγRIIIa(V), or human C1q; wherein the cancer is bladder cancer, breast cancer, biliary tract cancer, colon cancer, endometrial cancer, esophageal cancer, gastric cancer, head and neck cancer, non-small cell lung cancer, prostate cancer, rectal cancer, or thyroid cancer.

The present disclosure provides an antibody that is an agonist of human CD137 (SEQ ID NO:1), wherein the antibody comprises a heavy chain and a light chain; wherein the heavy chain contacts at least one amino acid residue of the following on human CD137: 55, 59, 63, 66, 72, 93-103 (inclusive), and 112-116 (inclusive); wherein the light chain contacts at least one amino acid residue of the following on human CD137: 96-98 (inclusive), 100, and 114-116 (inclusive).

The present disclosure provides an antibody that is an agonist of human CD137 (SEQ ID NO:1), wherein the antibody comprises a heavy chain and a light chain; wherein the heavy chain contacts at least one amino acid residue of the following on human CD137: 55, 59, 63, 66, 72, 93-103 (inclusive), and 112-116 (inclusive); wherein the light chain contacts at least one amino acid residue of the following on human CD137: 96-98 (inclusive), 100, and 114-116 (inclusive); wherein the residues in contact are within six (6) angstroms or less of the antibody, as determined by X-ray crystallography.

The present disclosure provides an antibody that is an agonist of human CD137 (SEQ ID NO:1), wherein the antibody comprises a heavy chain and a light chain; wherein the heavy chain contacts the following amino acid residues on human CD137: 55, 59, 63, 66, 72, 93-103 (inclusive), and 112-116 (inclusive); wherein the light chain contacts the following amino acid residues on human CD137: 96-98 (inclusive), 100, and 114-116 (inclusive); wherein the resi-dues in contact are within six (6) angstroms or less of the antibody, as determined by X-ray crystallography.

The present disclosure provides an antibody that is an agonist of human CD137 (SEQ ID NO:1), wherein the antibody comprises a heavy chain and a light chain; wherein the heavy chain contacts the following amino acid residues on human CD137: 55, 59, 63, 66, 72, 93-103 (inclusive), and 112-116 (inclusive); optionally, wherein the light chain contacts the following amino acid residues on human CD137: 96-98 (inclusive), 100, and 114-116 (inclusive).

The present disclosure provides an antibody that is an agonist of human CD137 (SEQ ID NO:1), wherein the antibody comprises a heavy chain and a light chain; wherein the heavy chain contacts the following amino acid residues on human CD137: 55, 59, 63, 66, 72, 93-103 (inclusive), and 112-116 (inclusive); optionally, wherein the light chain contacts the following amino acid residues on human CD137: 96-98 (inclusive), 100, and 114-116 (inclusive); wherein the residues in contact are within six (6) angstroms or less of the antibody, as determined by X-ray crystallography.

The present disclosure provides an antibody that is an agonist of human CD137 (SEQ ID NO:1) for use in the treatment of cancer, wherein the antibody comprises a heavy chain and a light chain; wherein the heavy chain contacts the following amino acid residues on human CD137: 55, 59, 63, 66, 72, 93-103 (inclusive), and 112-116 (inclusive); optionally, wherein the light chain contacts the following amino acid residues on human CD137: 96-98 (inclusive), 100, and 114-116 (inclusive); wherein the residues in contact are within six (6) angstroms or less of the antibody, as determined by X-ray crystallography.

The present disclosure provides the use of an antibody that is an agonist of human CD137 (SEQ ID NO:1) for the manufacture of a medicament for the treatment of cancer, wherein the antibody comprises a heavy chain and a light chain; wherein the heavy chain contacts the following amino acid residues on human CD137: 55, 59, 63, 66, 72, 93-103 (inclusive), and 112-116 (inclusive); optionally, wherein the light chain contacts the following amino acid residues on human CD137: 96-98 (inclusive), 100, and 114-116 (inclusive); wherein the residues in contact are within six (6) angstroms or less of the antibody, as determined by X-ray crystallography.

The present disclosure provides an antibody that is an agonist of human CD137 (SEQ ID NO:1) for use in the treatment of cancer, wherein the antibody comprises a heavy chain and a light chain; wherein the heavy chain contacts the following amino acid residues on human CD137: 55, 59, 63, 66, 72, 93-103 (inclusive), and 112-116 (inclusive); optionally, wherein the light chain contacts the following amino acid residues on human CD137: 96-98 (inclusive), 100, and 114-116 (inclusive); wherein the residues in contact are within six (6) angstroms or less of the antibody, as determined by X-ray crystallography; wherein the cancer is bladder cancer, breast cancer, biliary tract cancer, colon cancer, endometrial cancer, esophageal cancer, gastric cancer, head and neck cancer, non-small cell lung cancer, prostate cancer, rectal cancer, or thyroid cancer.

The present disclosure provides the use of an antibody that is an agonist of human CD137 (SEQ ID NO:1) for manufacture of a medicament for the treatment of cancer, wherein the antibody comprises a heavy chain and a light chain; wherein the heavy chain contacts the following amino acid residues on human CD137: 55, 59, 63, 66, 72, 93-103 (inclusive), and 112-116 (inclusive); optionally, wherein the light chain contacts the following amino acid residues on human CD137: 96-98 (inclusive), 100, and 114-116 (inclusive); wherein the residues in contact are within six (6) angstroms or less of the antibody, as determined by X-ray crystallography; wherein the cancer is bladder cancer, breast cancer, biliary tract cancer, colon cancer, endometrial cancer, esophageal cancer, gastric cancer, head and neck cancer, non-small cell lung cancer, prostate cancer, rectal cancer, or thyroid cancer.

The present disclosure provides an antibody that is an agonist of human CD137 (SEQ ID NO:1), wherein the antibody binds at least one of the following amino acid residues on human CD137: 97 and 115.

The present disclosure provides an antibody that is an agonist of human CD137 (SEQ ID NO:1), wherein the antibody binds at least two of the amino acid residues on human CD137: 97, 114, and 115.

The present disclosure provides an antibody that is an agonist of human CD137 (SEQ ID NO:1), wherein the antibody binds to the following amino acid residues on human CD137: 97, 114, and 115.

The present disclosure provides an antibody that is an agonist of human CD137 (SEQ ID NO:1), wherein the antibody binds at least one of the following amino acid residues on human CD137: 97 and 115; wherein binding is determined using a mutant human CD137 protein having a mutation at one or more of the following amino acid residues: 97, 114, and 115.

The present disclosure provides an antibody that is an agonist of human CD137 (SEQ ID NO:1), wherein the antibody binds at least two of the following amino acid residues on human CD137: 97, 114, and 115; wherein binding is determined using a mutant human CD137 protein having a mutation at one or more of the following amino acid residues: 97, 114, and 115.

The present disclosure provides an antibody that is an agonist of human CD137 (SEQ ID NO:1) for use in the treatment of cancer, wherein the antibody binds to the following amino acid residues on human CD137: 97, 114, and 115; wherein binding is determined using a mutant human CD137 protein having a mutation at one or more of the following amino acid residues: 97, 114, and 115.

The present disclosure provides the use of an antibody that is an agonist of human CD137 (SEQ ID NO:1) for the manufacture of a medicament for the treatment of cancer, wherein the antibody binds to the following amino acid residues on human CD137: 97, 114, and 115; wherein binding is determined using a mutant human CD137 protein having a mutation at one or more of the following amino acid residues: 97, 114, and 115.

The present disclosure provides an antibody that is an agonist of human CD137 (SEQ ID NO:1) for use in the treatment of cancer, wherein the antibody binds to the following amino acid residues on human CD137: 97, 114, and 115; wherein binding is determined using a mutant human CD137 protein having a mutation at one or more of the following amino acid residues: 97, 114, and 115; wherein the cancer is bladder cancer, breast cancer, biliary tract cancer, colon cancer, endometrial cancer, esophageal cancer, gastric cancer, head and neck cancer, non-small cell lung cancer, prostate cancer, rectal cancer, or thyroid cancer.

The present disclosure provides the use of an antibody that is an agonist of human CD137 (SEQ ID NO:1) for the manufacture of a medicament for the treatment of cancer, wherein the antibody binds to the following amino acid residues on human CD137: 97, 114, and 115; wherein binding is determined using a mutant human CD137 protein having a mutation at one or more of the following amino acid residues: 97, 114, and 115; wherein the cancer is bladder cancer, breast cancer, biliary tract cancer, colon cancer, endometrial cancer, esophageal cancer, gastric cancer, head and neck cancer, non-small cell lung cancer, prostate cancer, rectal cancer, or thyroid cancer.

The present disclosure provides a fully human CD137 agonist antibody comprising two or more of the following features: (a) the antibody competes with human CD137-Ligand for binding to human CD137; (b) the antibody does not bind human FcγRT, human FcγRIIa, human FcγRIIb, human FcγRIIIa(F), human FcγRIIIa(V), or human C1q; (c) the antibody binds to cynomolgus monkey CD137; (d) the antibody inhibits human non-small cell lung tumor growth as a monotherapy; and (e) the antibody increases the frequency of intratumoral $CD3^+$ T cells.

Non-limiting examples of useful chemotherapeutic agents include 5-fluorouracil, hydroxyurea, gemcitabine, methotrexate, doxorubicin, etoposide, carboplatin, cisplatin, cyclophosphamide, melphalan, dacarbazine, taxol, camptothecin, FOLFIRI, FOLFOX, docetaxel, daunorubicin, paclitaxel, oxaliplatin, and combinations thereof.

The term "antibody" as used herein refers to a polypeptide complex having two heavy chains (HC) and two light chains (LC) such that the heavy chains and lights chains are interconnected by disulfide bonds; wherein the antibody is an IgG subclass antibody.

An antibody of the present invention is an engineered, non-naturally occurring polypeptide complex. A DNA molecule of the present invention is a DNA molecule that comprises a non-naturally occurring polynucleotide sequence encoding a polypeptide having the amino acid sequence of at least one of the polypeptides in an antibody of the present invention.

The antibody of the present invention is an IgG type antibody and has "heavy" chains and "light" chains that are cross-linked via intra- and inter-chain disulfide bonds. Each heavy chain is comprised of an N-terminal HCVR and a heavy chain constant region ("HCCR"). Each light chain is comprised of a LCVR and a light chain constant region ("LCCR"). When expressed in certain biological systems, antibodies having native human Fc sequences are glycosylated in the Fc region. Typically, glycosylation occurs in the Fc region of the antibody at a highly conserved N-glycosylation site. N-glycans typically attach to asparagine. Antibodies may be glycosylated at other positions as well.

Optionally, the anti-human CD137 antibodies described herein contain an Fc portion that is derived from human IgG1. IgG1 is well known to bind to the proteins of the Fc-gamma receptor family (FcγR) as well as C1q. Interaction with these receptors can induce antibody-dependent cell cytotoxicity (ADCC) and complement-dependent cytotoxicity (CDC). Therefore, optionally, the anti-human CD137 antibodies described herein are a fully human monoclonal antibody lacking Fc effector function (IgG1, Fc-null). To achieve an Fc-null IgG1 antibody, selective mutagenesis of residues is necessary within the CH2 region of its IgG1 Fc region. Amino acid substitutions L234A, L235E, and G237A are introduced into IgG1 Fc to reduce binding to FcγRI, FcγRIIa, and FcγRIII, and substitutions A330S and P331S are introduced to reduce C1q-mediated complement fixation. To reduce the potential induction of an immune response when dosed in humans, certain amino acids may require back-mutations to match antibody germline sequences.

The HCVR and LCVR regions can be further subdivided into regions of hyper-variability, termed complementarity determining regions ("CDRs"), interspersed with regions that are more conserved, termed framework regions ("FR"). Each HCVR and LCVR is composed of three CDRs and four FRs, arranged from amino-terminus to carboxy-terminus in the following order: FR1, CDR1, FR2, CDR2, FR3, CDR3, FR4. Herein, the three CDRs of the heavy chain are referred to as "HCDR1, HCDR2, and HCDR3" and the three CDRs of the light chain are referred to as "LCDR1, LCDR2 and LCDR3". The CDRs contain most of the residues which form specific interactions with the antigen. For the purposes of the present invention, the North CDR definitions are used. The North CDR definition (North et al., "A New Clustering of Antibody CDR Loop Conformations", Journal of Molecular Biology, 406, 228-256 (2011)) is based on affinity propagation clustering with a large number of crystal structures.

An isolated DNA encoding a HCVR region can be converted to a full-length heavy chain gene by operably linking the HCVR-encoding DNA to another DNA molecule encoding heavy chain constant regions. The sequences of human, as well as other mammalian, heavy chain constant region genes are known in the art. DNA fragments encompassing these regions can be obtained e.g., by standard PCR amplification.

An isolated DNA encoding a LCVR region may be converted to a full-length light chain gene by operably linking the LCVR-encoding DNA to another DNA molecule encoding a light chain constant region. The sequences of human, as well as other mammalian, light chain constant region genes are known in the art. DNA fragments encompassing these regions can be obtained by standard PCR amplification. The light chain constant region can be a kappa or lambda constant region. Preferably for antibodies of the present invention, the light chain constant region is a kappa constant region.

The polynucleotides of the present invention will be expressed in a host cell after the sequences have been operably linked to an expression control sequence. The expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences.

The antibody of the present invention may readily be produced in mammalian cells, non-limiting examples of which includes CHO, NS0, HEK293 or COS cells. The host cells are cultured using techniques well known in the art.

The vectors containing the polynucleotide sequences of interest (e.g., the polynucleotides encoding the polypeptides of the antibody and expression control sequences) can be transferred into the host cell by well-known methods, which vary depending on the type of cellular host.

Various methods of protein purification may be employed and such methods are known in the art and described, for example, in Deutscher, *Methods in Enzymology* 182: 83-89 (1990) and Scopes, *Protein Purification: Principles and Practice,* 3rd Edition, Springer, N.Y. (1994).

In other embodiments of the present invention, the antibody, or the nucleic acids encoding the same, is provided in isolated form. As used herein, the term "isolated" refers to a protein, peptide, or nucleic acid which is free or substantially free from any other macromolecular species found in a cellular environment. "Substantially free" as used herein means the protein, peptide, or nucleic acid of interest comprises more than 80% (on a molar basis) of the macromolecular species present, preferably more than 90%, and more preferably more than 95%.

The antibody of the present invention, or pharmaceutical compositions comprising the same, may be administered by parenteral routes, a non-limiting example of which is intravenous administration. An antibody of the present invention may be administered to a patient alone with pharmaceutically acceptable carriers, diluents, or excipients in single or multiple doses. Pharmaceutical compositions of the present invention can be prepared by methods well known in the art (e.g., *Remington: The Science and Practice of Pharmacy,* $22^{nd}$ ed. (2012), A. Loyd et al., Pharmaceutical Press) and comprise an antibody, as disclosed herein, and one or more pharmaceutically acceptable carriers, diluents, or excipients.

Dosage regimens may be adjusted to provide the optimum desired response (e.g., a therapeutic effect). Treatment dosages may be titrated to optimize safety and efficacy. Dosing schedules, for intravenous (i.v.) or non-intravenous administration, localized or systemic, or combinations thereof, will typically range from a single bolus dosage or continuous infusion to multiple administrations per day (e.g., every 4-6 hours), or as indicated by the treating physician and the patient's condition. Dosing amounts and frequencies may be determined by the physicians treating the patient.

The term "treating" (or "treat" or "treatment") refers to slowing, interrupting, arresting, alleviating, stopping, reducing, or reversing the progression or severity of an existing symptom, disorder, condition, or disease.

"Effective amount" means the amount of an antibody of the present invention or pharmaceutical composition comprising an antibody of the present invention that will elicit the biological or medical response of or desired therapeutic effect on a tissue, system, animal, mammal or human that is being sought by the researcher, medical doctor, or other clinician. An effective amount of the antibody may vary according to factors such as the disease state, age, sex, and weight of the individual, and the ability of the antibody to elicit a desired response in the individual. An effective amount is also one in which any toxic or detrimental effect of the antibody is outweighed by the therapeutically beneficial effects.

ANTIBODY CHARACTERIZATION, GENERATION, EXPRESSION, AND PURIFICATION

Antibody production using the heavy chain polynucleotide sequence shown in SEQ ID NO: 14, and the light chain polynucleotide sequence shown in SEQ ID NO: 17 in mammalian cells results in the production of two antibody product-related species: (a) a full length antibody (hereafter referred to as "Antibody A1") having the heavy chain amino acid sequence shown in SEQ ID NO: 10 and the light chain amino acid sequence of SEQ ID NO: 11; and (b) a single amino acid truncated form of the antibody (hereafter referred to as "Antibody A2") resulting from the clipping of the n-terminal alanine of the light chain, the Antibody A2 having the heavy chain amino acid sequence shown in SEQ ID NO: 10 and the light chain amino acid sequence shown in SEQ ID NO: 13. As used herein, "Antibody A1/2" refers to the antibody product that results from the use of the light chain polynucleotide sequence shown in SEQ ID NO: 17 and includes a combination of Antibody A1 (~6%) and Antibody A2 (~94%). Antibody A1 can be synthesized without significant quantities of Antibody A2 using the heavy chain polynucleotide sequence shown in SEQ ID NO: 14 and the light chain polynucleotide sequence shown in SEQ ID NO: 15. Antibody A2 can be synthesized without significant quantities of Antibody A1 using the heavy chain polynucleotide sequence shown in SEQ ID NO: 14 and the light chain polynucleotide sequence shown in SEQ ID NO: 16.

The antibodies of the present invention may be generated by using known methods, including but not limited to, phage display. Additionally, the antibodies derived as described above may be further screened using the assays described herein.

The polypeptides of the variable regions of the heavy chain and light chain and the complete heavy chain and light chain amino acid sequences of Antibodies A1 and A2, and the nucleotide sequences encoding the same, are listed in the section entitled "Amino Acid and Nucleotide Sequences." In addition, the SEQ ID NOs for the light chain, heavy chain, light chain variable region, and heavy chain variable region of Antibodies A1, A2, and A1/2 are shown in Tables 1 & 2.

TABLE 1

| Corresponding SEQ ID (Amino Acid) | Antibody A1 | Antibody A2 |
|---|---|---|
| HCDR1 | 2 | 2 |
| HCDR2 | 3 | 3 |
| HCDR3 | 4 | 4 |
| LCDR1 | 5 | 5 |
| LCDR2 | 6 | 6 |
| LCDR3 | 7 | 7 |
| HCVR | 8 | 8 |
| LCVR | 9 | 12 |
| Heavy chain | 10 | 10 |
| Light chain | 11 | 13 |

TABLE 2

| Corresponding SEQ ID (DNA) | Antibody A1 | Antibody A2 | Antibody A1/2 |
|---|---|---|---|
| HC | 14 | 14 | 14 |
| LC | 15 | 16 | 17 |

The antibodies of the present invention, including, but not limited to, Antibodies A1, A2, and A1/2 can be made and purified essentially as follows. An appropriate host cell, such as HEK 293 or CHO, can be either transiently or stably transfected with an expression system for secreting antibodies using an optimal predetermined HC:LC vector ratio or a single vector system encoding both HC and LC. Clarified media, into which the antibody has been secreted, may be purified using any of many commonly-used techniques. For example, the medium may be conveniently applied to a MabSelect column (GE Healthcare), or KappaSelect column (GE Healthcare), that has been equilibrated with a compatible buffer, such as phosphate buffered saline (pH 7.4). The column may be washed to remove nonspecific binding components. The bound antibody may be eluted, for example, by pH gradient (such as 20 mM Tris buffer pH 7 to 10 mM sodium citrate buffer pH 3.0, or phosphate buffered saline pH 7.4 to 100 mM glycine buffer pH 3.0). Antibody fractions may be detected, such as by UV absorbance or SDS-PAGE, and then may be pooled. Further purification is optional, depending on the intended use. The antibody may be concentrated and/or sterile filtered using common techniques. Soluble aggregate and multimers may be effectively removed by common techniques, including size exclusion, hydrophobic interaction, ion exchange, multimodal, or hydroxyapatite chromatography. The product may be immediately frozen at −70° C. or may be lyophilized.

As used herein, BMS20H4.9 refers to an antibody having the heavy chain shown in SEQ ID NO: 18 and the light chain shown in SEQ ID NO: 19, and has been previously described in U.S. Pat. No. 7,288,638. As used herein, PF83 refers to an antibody having the heavy chain shown in SEQ ID NO: 20 and the light chain shown in SEQ ID NO: 21, and has been previously described in U.S. Pat. No. 8,337,850.

Antibody A1/2 Binds to Human CD137

The ability of the antibodies disclosed herein to bind human CD137 can be measured by ELISA. To measure binding to human CD137, a 96-well plate (Nunc) is coated with human CD137-Fc (R&D Systems) overnight at 4° C. Wells are blocked for 2 h with blocking buffer (PBS containing 0.2% bovine serum albumin and 0.05% Tween-20). Wells are washed three times with PBS containing 0.05% Tween-20. Antibody A1/2 or control IgG (100 microliters) is then added at different concentrations and incubated at room temperature for 1 h. After washing, the plate is incubated with 100 microliters of goat anti-human IgG F(ab')2-HRP conjugate (Jackson Immuno Research Laboratories) at room temperature for 45 minutes. The plates are washed and then incubated with 100 microliters of 3,3', 5,5'-tetra-methylbenzidine. The absorbance at 650 nm is read on a SpectraMax® microplate reader. The half maximal effective concentration ($EC_{50}$) is calculated using GraphPad Prism 7 software.

In experiments performed essentially as described above, Antibody A1/2 binds human CD137 with an $EC_{50}$ of 0.027 nM.

Antibody A1/2 Binds to Cynomolgus Monkey CD137

The ability of the antibodies disclosed herein to bind to cell surface cynomolgus monkey CD137 can be measured using a flow cytometric assay. Cynomolgus monkey CD137 expressing stable cells are generated by transfecting Cyno-CD137 receptor plasmid DNA into human 293 cells (ATCC) using Lipofectamine™ 2000 reagent (Invitrogen™) per manufacturer's protocol. Stable cells are selected using 0.5 micrograms/mL puromycin in Dulbecoo's Modified Eagle's Medium containing 10% fetal bovine serum and 1% GlutaMAX™. For flow cytometry, confluent adherent cells are detached using Gibco® Cell Dissociation Buffer (Life Technologies), blocked in FACS buffer (phosphate buffered saline containing 3% fetal bovine serum) for 1 h at 4° C., and then transferred into a 96-well round-bottom plate at a density of $1 \times 10^5$ cells/well. Antibody A1/2, BMS20H4.9, PF83, or control human IgG1 (diluted in FACS buffer 1:4 starting at 0.5 micrograms/mL) are added (100 microliters) and cells are stained for 1 h at 4° C.

After washing in FACS buffer, secondary antibody R-phycoerythrin conjugated goat anti-human IgG, F(ab')2 fragment specific antibody (Jackson ImmunoResearch Laboratories) is added at a 1:200 dilution and cells are incubated at 4° C. for 30 minutes. Cells are washed and live/dead cell staining is performed using LIVE/DEAD® Fixable Far Red Dead Cell Stain kit (Life Technologies) per manufacturer's protocol. Cells are washed in FACS buffer and processed on an IntelliCyt HTFC® Screening System. Flow cytometry data is analyzed using FlowJo® Software. Mean fluorescence intensity (MFI) ratio is calculated as the (MFI of Experimental antibody)/(MFI of the control IgG).

In experiments performed essentially as described above, Antibody A1/2 at a concentration of 0.5 micrograms/mL displays a higher MFI ratio of 153 as compared to BMS20H4.9 (MFI ratio of 0.94) and PF83 (MFI ratio of 37).

Antibody A1/2 Binding on Human Cells Increases CD137 Expression

The ability of the antibodies disclosed herein to modulate human CD137 cell surface levels can be determined as follows. Human CD137 expressing stable cells are generated by transfecting human CD137 plasmid DNA into human 293 cells (ATCC) using Lipofectamine™ 2000 reagent (Invitrogen™) per manufacturer's protocol. Stable cells are selected using 0.5 micrograms/mL of puromycin in Dulbecoo's Modified Eagle's Medium containing 10% fetal bovine serum and 1% GlutaMAX™. CD137 antibodies starting at 300 nanomolar in media are incubated with the cells at 37° C. for 24 hr. The cells are washed with PBS, detached using Gibco® Cell Dissociation Buffer, and stained with the same CD137 antibodies in cold buffer (1×PBS, 1% BSA, 0.09% sodium azide) for 2 h. After washing, cells are stained with Alexa Fluor 647-conjugated goat anti-human IgG detection antibody (Jackson ImmunoResearch Laboratories) for 30 minutes. Cells are washed and differentially labeled with Zombie Green Live/Dead (BioLegend) per manufacturer's protocol. All cells are processed on a Fortessa X-20. Analysis is performed with FlowJo® Software to generate Median Fluorescence Intensity (MFI) of Alexa Fluor 647 and calibrated to an Alexa Fluor 647 molecules of equivalent soluble fluorochrome (MESF) standard curve (Bangs Laboratories). MESF values are normalized to untreated stained controls (100%) and untreated isotype stained controls (0%).

In experiments performed essentially as described above, Antibody A1/2 at a concentration of 300 nanomolar induces an increase (21%) in CD137 levels compared to PF83 (12%) whereas BMS20H4.9 reduces CD137 on the cell surface by 56%. NF-kappaB Luciferase Reporter Assay Activity of Antibody A1/2

The ability of the antibodies disclosed herein to activate NF-kappaB can be measured as follows. Double stable NF-kappaB luciferase reporter/human CD137-293 cells are generated by transfecting pGL4.32[luc2P/NF-kappaB-RE/Hygro] plasmid DNA (Promega) into human CD137-expressing 293 cells using Lipofectamine™ 2000 Reagent (Life Technologies) per manufacturer's protocol. Stable cells are selected using 100 micrograms/mL hygromycin and 0.5 micrograms/mL puromycin in Dulbecoo's Modified Eagle's Medium containing 10% fetal bovine serum and 1% GlutaMAX™. Cells are plated in a 384 well plate at a density of $5 \times 10^3$ cells/well using the Thermo MultiDrop Combi Reagent Dispenser (Thermo Fisher Scientific) and cultured overnight at 37° C. Antibody A1/2, BMS20H4.9, PF83, or control human IgG1 are diluted in phosphate buffered saline (PBS) using Hamilton STAR™ (Hamilton Company) at 10-point 2-fold dilutions within the plate starting at 9 micromolar or 1.33 micromolar and transferred to cells. Cells are then incubated with the antibodies for 5.5 h at 37° C. in 5% $CO_2$ and then processed using the ONE-Glo™ Luciferase Assay System (Promega™) and Thermo™ Scientifi MultiDrop™ Combi Reagent Dispenser. Luminescence is measured using a SpectraMax® microplate reader (Molecular Devices) and data analysis is performed using a Genedata Screener® (Genedata). Data is normalized as follows: % Activity=[(Well Value-Median of Minimum Control)/(Median of Maximum Control-Median of Minimum Control)]×100%.

In experiments performed essentially as described above, Antibody A1/2 displays a max activity of 78% that is higher than PF83 (max activity of 12%) and lower than BMS20H4.9 (max activity of 115%).

Antibody A1/2 Promotes T Cell-Derived Interferon-Gamma Production

The ability of the antibodies disclosed herein to promote T cell-derived interferon-gamma (IFN-gamma) production can be measured as follows. Human peripheral blood mononuclear cells (PBMCs) are isolated from whole blood or leukopacs by Ficoll density gradient centrifugation (Ficoll® Paque PLUS; GE Healthcare) and grown in Roswell Park Memorial Institute medium (RPMI) (Life Technologies) with 10% fetal calf serum (HyClone). Anti-human CD3 antibody clone HIT3a (BD Biosciences) in PBS is coated onto a 96-well plate (typical range: 2 to 15 nanograms/well) and incubated overnight at 4° C. After aspirating, wells are rinsed with PBS and human PBMCs are transferred onto a 96-well plate at a density of $1.5 \times 10^5$ cells/well. Antibody A1/2, BMS20H4.9, PF83, or control human IgG1 are prepared by diluting 1:4 in RPMI containing 10% fetal bovine serum at a starting concentration of 80 micrograms/mL. Anti-human CD28 antibody clone CD28.2 (BioLegend) is added to the plate (typical range 0.2 to 2 micrograms/mL) followed by the test antibody and incubated for 96 h at 37° C. in a humidified 5% $CO_2$ incubator. Supernatants are collected and human IFN-gamma levels are measured using a R&D Systems® human IFN-gamma DuoSet ELISA Kit. Briefly, IFN-gamma capture antibody is coated onto plate (4 micrograms/mL) overnight at room temperature. After aspirating and washing, the plate is blocked for 1 h at room temperature. Sample supernatants and IFN-gamma standard are added and incubated for 2 h at room temperature. After washing, 100 microliters of IFN-gamma detection antibody is added, incubated for 2 hr at room temperature, and washed. Streptavidin-HRP (100 microliters of 1:40 dilution) is added for 20 minutes at room temperature. After washing, plates are developed by adding 100 microliters substrate solution for 20 minutes followed by 50 microliters stop solution, and the signal is measured at 450 nm with SpectraMax® microplate reader. Data analysis is performed using SoftMax Pro software and GraphPad Prism (GraphPad Software). Fold induction is calculated as sample mean IFN-gamma (pg/mL)/Control hIgG1 mean IFN-gamma (pg/mL).

In experiments performed essentially as described above, Antibody A1/2 enhances the sub-optimal activation of human PBMCs by CD3/CD28 co-stimulation as measured by IFN-gamma cytokine production. In this regard, treatment with Antibody A1/2 at 5 micrograms/ml results in a 3.8-fold increase in the production of IFN-gamma that was higher than PF83 (1.6-fold increase) and lower than BMS20H4.9 (9.4-fold increase).

Antibody A1/2 Solid-Phase Binding Assay

The binding of Antibody A1/2 to human C1q can be measured using an ELISA assay. Antibody A1/2 and control antibodies (negative control IgG1) are serially diluted in PBS and coated onto an ELISA plate overnight at 4° C. Human C1q in casein buffer is added at a concentration of 10 milligrams/mL and incubated for 2 hrs. Human C1q is detected by incubating the plates with anti-human C1q-HRP (AbD Serotec Inc., 1:200 dilution) for 1 h and the plate is developed using TMB (KPL, Inc.). Absorbance is measured at 450 nm with Synergy Neo2 hybrid multi-mode reader (BioTek®).

The binding of Antibody A1/2 to FcγRI, FcγRIIa(H), FcγRIIb, FcγRIIIa(F), and FcγRIIIa(V) is determined using an MSD assay (Meso Scale Diagnostics). Briefly, Fcγ receptors are coated onto a Meso Scale plate overnight and serially diluted test antibodies are added to the plate and incubated for 2 h. Antibody A1/2 is detected using an anti-human secondary antibody (Meso Scale Diagnostics, D20TF-6) and the plate is developed with Read Buffer T (Meso Scale Diagnostics, R92TC-1). Luminescence is measured on a SECTOR Imager 2400 (Meso Scale Diagnostics) and data is analyzed using GraphPad Prism 7.0 software.

TABLE 3

| Antibody | FcγRI (EC$_{50}$ nM) | FcγRIIa(H) (EC$_{50}$ nM) | FcγRIIb (EC$_{50}$ nM) | FcγRIIIa(F) (EC$_{50}$ nM) | FcγRIIIa(V) (EC$_{50}$ nM) | Human C1q (EC$_{50}$ nM) |
|---|---|---|---|---|---|---|
| Antibody A1/2 | >5* | >134* | >134* | >134* | >134* | >330* |
| Positive Control IgG1 (Intact Fc receptor effector functionality) | 0.8 | 93.7 | >134* | 19 | 6.2 | 8.9 |

*Denotes the maximum concentration of the antibody tested

In experiments performed essentially as described above, Antibody A1/2 did not bind to FcγRI, FcγRIIa, FcγRIIb, FcγRIIIa, FcγRIIIa, or C1q (as shown in Table 3 above). In other experiments, Antibody A1/2 exhibited no detectable effector function in cell-based antibody-dependent cellular cytotoxicity and complement-dependent cytotoxicity assays.

Antitumor Efficacy of Antibody A1/2 in an Established Tumor Model

The HCC827 human non-small cell lung cancer (ATCC) tumor cell line is maintained in its respective media and harvested for implantation. Tumor cells (1×10$^7$ cells per mouse) are injected subcutaneously into the right flank of female NOD/SCID Gamma (NSG) mice at 7 weeks of age (Jackson Laboratories). When tumors reach approximately 350 mm$^3$ to 450 mm$^3$ in size, mice are randomized into groups of 5 to 8. Human expanded T cells are generated by stimulating naïve human PBMCs with Dynabeads® Human T-expander CD3/CD28 beads (Thermo Fisher Scientific) for 9 to 10 days and banked. Human PBMCs (NY Blood Center) are prepared by centrifugation over Ficoll® Paque PLUS in SepMate tubes (STEMCELL Technologies) and banked. Expanded T cells are thawed and 1×10$^6$ cells are injected into the mice. As a control, tumor cells alone are implanted with no T cells or PBMCs in some mice. Treatment starts at either Day 0 or Day 1. Treatment groups include control IgG, BMS20H4.9, PF83, and Antibody A1/2. Animals are dosed via intraperitoneal injection at 10 mg/kg of antibody once weekly for 4 weeks. Body weight (BW) is recorded twice a week and the percent change in BW is calculated using the formula: (BW on observation day−BW on initial day)/BW initial day×100%. Tumor volumes are measured twice per week using electronic calipers. Tumor volume is calculated using the formula: Tumor Volume (mm$^3$)=π/6*Length*Width$^2$. The % T/C is calculated using the formula 100×ΔT/ΔC if ΔT>0 of the geometric mean values. ΔT=mean tumor volume of the drug-treated group on the observation day of the study−mean tumor volume of the drug-treated group on initial day of dosing; ΔC=mean tumor volume of the control group on the observation day of the study−mean tumor volume of the control group on initial day of dosing. Statistical analysis of tumor volume data is performed by two-way repeated measures analysis of variance by time and treatment using the MIXED procedures in SAS software (Version 9.2).

In experiments performed essentially as described above, mice treated with Antibody A1/2 demonstrated significant tumor growth inhibition (T/C %=30.6; P<0.001) in contrast to mice treated with PF83 (T/C %=81.2) and BMS20H4.9 (T/C %=96.9) which showed no inhibition.

Kinetics/Affinity Results for Antibody A1, Antibody A2, and Antibody A1/2

A Biacore T200 instrument can be used to measure the kinetics of immobilized human CD137-Fc binding to Antibody A1, Antibody A2, and Antibody A1/2. Recombinant human extracellular CD137-Fc protein (R&D Systems) is covalently immobilized to a CMS sensor chip via amine coupling (GE Healthcare). CD137 antibody testing is performed at a flow rate of 30 microliters/min in HBS-EP+ buffer. Samples are injected at various concentrations and measurements obtained at 25° C. The surface is regenerated after each sample injection with 10 millimolar Glycine-HCl pH2.0 at flow rate of 30 microliters/min for 24 seconds and then stabilized with buffer for 10 seconds. Sensorgrams of concentrations ranging from 0.123 nanomolar to 30 nanomolar are evaluated using Biacore T200 software. Calculation of association (Ka) and dissociation (Kd) rate constants are based on a 1:1 Langmuir binding model fit. The equilibrium dissociation constant (KD) or binding affinity constant is calculated from the ratio of kinetic rate constants Kd/Ka.

In experiments performed essentially as described above, Antibody A1, Antibody A2, and Antibody A1/2 bind to human CD137 with the kinetics and affinity constants illustrated in Table 4.

TABLE 4

| Antibody | K$_{on}$ (1/Ms) | K$_{off}$ (1/s) | K$_D$ (M) | R$_{max}$ | Chi$^2$ |
|---|---|---|---|---|---|
| Antibody A2 | 1.33E+06 | 7.13E−03 | 5.36E−09 | 23.10 | 0.247 |
| Antibody A1 | 1.61E+06 | 5.36E−03 | 3.33E−09 | 22.76 | 0.355 |
| Antibody A1/2 | 1.52E+06 | 7.11E−03 | 4.67E−09 | 20.86 | 0.303 |

NF-kappaB Luciferase Reporter Assay Comparing Antibody A1, Antibody A2, and Antibody A1/2

The ability of the antibodies disclosed herein to activate NF-kappaB can be measured as previously described herein with the modification that the antibody dilutions are prepared in PBS and 10-point 2-fold dilutions are made within the plate starting at 9 micromolar.

In experiments performed essentially as described above, Antibody A1/2 (max activity of 70.5%) displayed a similar max activity as compared to Antibody A1 (max activity of 63.4%) and Antibody A2 (max activity of 72.3%).

Antibody A1 and Antibody A2 Promote T Cell-Derived Interferon-Gamma Production

The ability of antibodies disclosed herein to promote T cell-derived interferon-gamma (IFN-gamma) production can be measured as previously described herein. In experiments performed essentially as described herein, Antibody A1, Antibody A2, and Antibody A1/2 enhance the suboptimal activation of human PBMCs by CD3/CD28 co-stimulation as measured by IFN-gamma cytokine production. In this regard, treatment with Antibody A1/2 at 5 micrograms/mL results in a 3.1-fold increase in the production of IFN-gamma that was comparable to Antibody A1 (3.5-fold increase) and Antibody A2 (3.5-fold increase).

Antitumor Efficacy of Antibody A1 and Antibody A2 in an Established Tumor Model

The ability of the antibodies disclosed herein to inhibit tumor growth in mice can be measured as previously described herein.

In experiments performed as essentially described above, Antibody A1, Antibody A2, and Antibody A1/2 inhibit tumor growth in the HCC827 established tumor model. Treatment with Antibody A1/2 (T/C %=47.1%; P<0.001) shows a similar reduction in tumor growth as Antibody A1 (T/C %=56.0%; P<0.001) and Antibody A2 (T/C %=48.7%; P<0.001).

Epitope of Antibody A1 as Determined Via X-Ray Crystallography

Antibody A1-Fab is purified from a 293HEK cell supernatant using a 12 mL CaptureSelect IgG-CH1 Affinity Matrix. SDS-PAGE and analytical size exclusion chromatography (SEC) are utilized to address the purity and quality of the purified Antibody A1-Fab. The eluted material of this matrix is buffer exchanged with 1×Tris-buffered saline (TBS). The hCD137* (*(human CD137 amino acids 22-161, AC121S)-AAA-6His) is purified from a 293HEK supernatant in three steps that utilize Ni Sepharose® Excel columns, Ni-NTA columns, and SEC columns. Briefly, two liters of supernatant is loaded directly without any buffer exchange into a Ni Sepharose Excel column. The elutant of this step is buffer exchanged with PBS and further purified using a Ni-NTA gravity flow column. The elutant of this step is further purified and buffer exchanged with 1×TBS using a preparatory SEC column. Flow through from the first Ni Sepharose Excel step contains significant amounts of hCD137*. It is then reloaded into a Ni Sepharose Excel column followed by the Ni-NTA and preparatory SEC columns. SDS-PAGE is used to pool the hCD137* fractions based on their purity. The concentration of hCD137* is 14.5 milligrams/mL and that of Antibody A1-Fab is 7.5 milligrams/mL.

The Antibody A1-Fab:CD137* complexes are combined at a 1:1 molar ratio and then subjected to a gel filtration column, pre-equilibrated in 20 millimolarTris pH 8.0, 100 millimolar sodium chloride. The resulting complex is concentrated to 12.5 milligrams/mL. After filtration, the Antibody A1-Fab:CD137 complex is set to a 1:1 ratio with sparse matrix crystal screening conditions in sitting drop plates using a Phoenix liquid handler, at both 21° C. and 8° C. Large, prism-like crystals grow in a single condition within 4 days in 1 molar Tri Sodium Citrate pH 6.5 at 21° C. Crystals are harvested and cryo-protected in 20% glycerol and reservoir conditions, mounted and flash-frozen in liquid nitrogen, then using an Advanced Photo Source, Argonne National Laboratory, samples are X-ray screened and the data is collected. The Antibody A1-Fab/hCD137* data is processed to 2.4 Å using the CCP4 suite of programs (Winn, M. D. et al. *Acta. Cryst.* 2011: D67, 235-242). The crystal belongs to Space Group P3121, with cell parameters a=b=124.9 Å, b=112.7 Å, α=β=90° and γ=120°. The structure is determined by Molecular Replacement with the program Phaser (McCoy, A. J. et al. *J. Appl. Cryst.* 2007 40: 658-674) using an internal Fab structure as a search model. The molecular replacement solution for the Fab is refined using Refmac (Winn, M. D. et al. *Acta. Cryst.* 2011: D67, 235-242; Murshudov, G. N. *Act. Cryst.* 2011: D67, 355-367) and Buster (Bricogne, G. et al. 2016; Buster Version 2.11.6. Cambridge, United Kingdom: Global Phasing Let.). Maps from the refinement are used to manually build in the model for CD137 using the program COOT (Emsley, P. Acta Cryst. 2010: D66, 486-501). The refined R-factors are R=17.8%, Rfree=20.5%.

In experiments performed essentially as described in this assay, Antibody A1-Fab:hCD137* complex is resolved and the epitope/paratope is illustrated in Table 5 below. Table 5 lists the residues on Antibody A1-Fab that are within 6 Å of the listed residues on hCD137*. The heavy chain of the Antibody A1-Fab has 57 contacts (cutoff 6 Å) with hCD137* while the light chain has 18 contacts (cutoff 6 Å).

TABLE 5

| Human CD137 (Epitope) | Antibody A1 Heavy Chain (Paratope) | Antibody A1 Light Chain (Paratope) |
| --- | --- | --- |
| S55 | Q62 | — |
| Q59 | Q62 | — |
| D63 | Q62 | — |
| R66 | F55 | — |
| F72 | F55 | — |
| H93 | T103 | — |
| C94 | T102, T103, A104, P105 | — |
| L95 | M101, T102, T103, P105, G106, T107 | — |
| G96 | L100, M101, T102, T103, P105, G106, T107 | G92, N93 |
| A97 | M101, T102, P105, G106, T107 | G92, N93, S94, F95, L97 |
| G98 | P105 | G92, N93, S94, F95 |
| C99 | P105 | — |
| S100 | I52, F55, N59, M101, P105, T107 | F95 |
| M101 | S31, I52, I54, F55, M101 | — |
| C102 | F55 | — |
| E103 | T103 | — |
| L112 | T103 | — |
| T113 | T103 | — |
| K114 | M101, T102, T103, A104 | D51, D54 |
| K115 | L100, M101, T102, T103, D110 | F50, E56, T57 |
| G116 | M101, T102, T103 | F50 |

Antibody A1/2 Completely Blocks CD137/CD137-Ligand Interactions

The ability of the antibodies disclosed herein to block human CD137 and CD137-Ligand (hereafter, CD137L) interactions can be measured with an ELISA assay. First, an ELISA assay is utilized to quantify the binding $EC_{50}$ of hCD137** (human CD137 amino acids 22-164, AC121S)-AAA-FLAG to hCD137L* and Antibody A1/2, BMS20H4.9 and PF83. The wells of a 96 well Immulon® 4HBX ELISA plate are coated overnight with 50 nanograms of hCD137** in 100 microliters of PBS, pH 7.2 with mild agitation at 4° C. After blocking with 5% BSA in PBST and washing, a five-fold dilution series (392 nanomlar-0.005 nanomolar) of His-tagged recombinant human CD137L (hereafter referred to as hCD137L*) (R&D Systems), (53–0.00068 nanomolar) of BMS20H4.9, (107–0.0014 nanomolar) of PF83, or (53–0.00068 nanomolar) of Antibody A1/2 are added with each dilution conducted in duplicate and incubated with mild agitation for 1 h at room temperature. The wells treated with the anti-CD137 antibodies are then washed and a 1:10000 dilution of HRP-conjugated goat anti-Fab antibody (Jackson ImmunoResearch Laboratories) is added and incubated at room temperature following standard protocol. The wells treated with hCD137L* are then washed and a 1:5000 dilution of HRP-conjugated mouse anti-His antibody (Sigma-Aldrich®) is added and the plates are incubated at room temperature following standard protocol. TMB peroxidase chromogenic substrate and stop solution are used according to manufacturer's instruction for visualization and detection of signals. Absorbance readings are plotted in GraphPad Prism Software Version 6. $EC_{50}$ values are calculated by nonlinear regression curve fit analysis of the software's One Site—Specific Binding function. In experiments performed as described, the binding affinities ($EC_{50}$) to hCD137** are determined as 0.6 nanomolar for hCD137L, 1.4 nanomolar for Antibody 1/2, 0.43 nanomolar for BMS20H4.9, and greater than 10 nanomolar for PF83.

The ability of hCD137L* to compete with BMS20H4.9, PF83, and Antibody A1/2 for binding to hCD137 can be determined as follows. A 96-well Immulon 4HBX ELISA plate is coated overnight with 50 nanograms of hCD137 in 100 microliters of PBS, pH 7.2 with mild agitation at 4° C. After blocking (with 5% BSA in PBST) and washing, a five-fold dilution (196 to 0.0025 nanomolar) of hCD137L* is mixed with saturating amounts of the designated antibody: Antibody A1/2 (200 nanograms/well), BMS20H4.9 (3 nanograms/well), or PF83 (1000 nanograms/well). The mixtures are then added to the wells in duplicates and incubated with mild agitation at room temperature for 1 h. After washing, the plate is incubated with HRP-conjugated goat anti-Fab antibody (1:1000 dilutions, Jackson ImmunoResearch Laboratories) at room temperature following standard protocol. TMB peroxidase chromogenic substrate and stop solution are used according to manufacturer's instruction for visualization and detection of signals.

The percentage of mAb that remains bound to CD137 is plotted and $IC_{50}$ values are calculated by nonlinear regression curve fit analysis using GraphPad Prism software. In experiments performed essentially as described above, hCD137L* fully blocks the binding of Antibody A1/2 to hCD137** with an $IC_{50}$ of 0.401 nanomolar. hCD137L* also blocks the binding of PF83 to hCD137** with an $IC_{50}$ of 1.037 nanomolar (30% binding signal remains on the surface). There is no measurable effect of hCD137L* on the binding of BMS20H4.9 to hCD137**.

Antibody A1/2 Binds Human CD137 at Specific Amino Acid Residues that are Distinct from BMS20H4.9 and PF83

Human CD137 point mutations are introduced to determine the amino acids residues where Antibody A1/2, BMS20H4.9, and PF83 bind to human CD137. The CD137-Fc mutants are generated using the standard protocol of a commercially-available site directed mutagenesis kit (Quickchange II kit, Qiagen). The wild-type and mutant CD137-Fc proteins are expressed and purified. All the mutants reported here have a size exclusion profile similar to that of the wild-type CD137-Fc (i.e. the mutations introduced do not compromise the structural integrity of the protein). To determine the impact of a mutation on the binding of the antibodies, a point ELISA assay against CD137-Fc wild type and mutants is utilized. The wells of a 96-well Immulon 4HBX ELISA plate are coated overnight with 50 nanograms of human CD137-ECD-C121S-Fc or its mutants in 100 microliters of PBS, pH 7.2 with mild agitation at 4° C. After blocking (with 5% BSA in PBST) and washing, a five-fold dilution eight-point series (100–0.00128 nanomolar) of the designated antibody is added and incubated with mild agitation at room temperature for 1 h. The wells are washed and a HRP-conjugated secondary antibody (1:10000 dilution of HRP-conjugated goat anti-Fab antibody (Jackson ImmunoResearch Laboratories) is added and incubated at room temperature following standard protocol. TMB peroxidase chromogenic substrate and stop solution are used according to manufacturer's instruction for visualization and detection of signals. Absorbance readings for each concentration point is normalized by the absorbance of the wild-type interaction. For each mutant, the mean of the normalized ratio for the eight concentrations is determined.

Mutations were individually introduced into human CD137 (SEQ ID NO: 1) at positions: P27, N42, D63, Q67, A97, G98, S100, M101, Q104, K114, K115, R130, I132, R134. Table 6 demonstrates the binding profiles of BMS20H4.9 and Antibody A1/2 for the shown mutants of human CD137. Table 7 demonstrates the binding profiles of PF83 and Antibody A1/2 for the shown mutants of human CD137. Collectively, Tables 6 and 7 demonstrate that Antibody A1/2 binds to distinct amino acid residues on human CD137 as compared to BMS20H4.9 and PF-83.

TABLE 6

|  | BMS20H4.9 (% of binding relative to wild-type hCD137) | Antibody A1/2 (% of binding relative to wild-type hCD137) |
| --- | --- | --- |
| P27L* | 85 | 100 |
| N42S* | 0 | 100 |
| D63N | 100 | 100 |
| Q67R | 100 | 100 |
| Q67V | 100 | 100 |
| A97P | 100 | 15 |
| G98K | 100 | 85 |
| G98Q | 100 | 100 |
| S100T | 100 | 100 |
| M101R | 100 | 100 |
| Q104K | 100 | 100 |
| K114E | 100 | 20 |
| K115Q | 100 | 25 |

*Denotes positions that are outside the epitope of Antibody A1/2 as determined via X-Ray Crystallography at 6 Å

TABLE 7

|  | Antibody A1/2 (% of binding relative to wild-type hCD137) | PF83 (% of binding relative to wild-type hCD137) |
| --- | --- | --- |
| K115Q | 25 | 100 |
| R130A* | 100 | 100 |
| R130H* | 100 | 100 |
| I132V* | 100 | 100 |
| R134Q* | 100 | 25 |

*Denotes positions that are outside the epitope of Antibody A1/2 as determined via X-Ray Crystallography at 6 Å

CD137 Gene Expression in Human Tumors

CD137 gene expression profile in human tumor immune infiltrates can be analyzed using The Cancer Genome Atlas (TCGA) database and computational methodologies. Briefly, expression ratios of CD137/CD3e are generated from Omicsoft curated TCGA RNASeq results. To compare the expression ratios of CD137/CD3e in tumor samples and adjacent normals of same tissue, a t-test is performed and Cohen's d is calculated for each tumor type. Tumor types that have a P value <0.05 in the t-test of expression ratio of tumor versus normal and a large effect size of Cohen's d>0.8 are statistically significant. The difference in expression ratio of CD137/CD3e in tumor versus normal tissue is calculated as the log fold change (log FC).

In experiments performed as described, an increased tumor CD137/CD3 ratio is observed across different cancer types, including, but not limited to, breast, colon, endometrial, bladder and head and neck (Table 8). Tumors enriched with CD137+ lymphocytes are candidates for CD137 antibody therapy using Antibody A1, Antibody A2 or Antibody A1/2.

TABLE 8

| Cancer | CD137/CD3 Expression Ratio (logFC) | P Value |
| --- | --- | --- |
| Bladder | 1.92 | 3.85E−03 |
| Breast | 2.46 | 3.56E−39 |
| Cholangiocarcinoma | 1.78 | 4.81E−06 |
| Colon | 2.36 | 1.23E−19 |
| Endometrial | 2.14 | 4.01E−15 |
| Esophageal | 1.07 | 1.71E−04 |
| Gastric | 1.68 | 9.27E−10 |
| Head & Neck | 1.90 | 8.06E−15 |
| Lung Adenocarcinoma | 1.37 | 2.63E−13 |
| Lung Squamous Cell Carcinoma | 1.63 | 2.37E−13 |
| Prostate | 1.04 | 2.73E−04 |
| Rectal | 1.62 | 1.40E−05 |
| Thyroid | 1.24 | 2.29E−06 |

Antibody A1/2 Increases $CD3^+$ T Cell Tumor Infiltration In Vivo

The ability of antibodies disclosed herein to alter T cell tumor infiltration in humanized mouse models can be determined by immunohistochemistry (IHC). Briefly, L55 human non-small cell lung cancer cells (L55-CBG-2A-GFP, University of Pennsylvania) are implanted in NSG mice. When tumors reach 250-300 $mm^3$-in size, human PBMCs ($8\times10^6$ cells) are injected and antibodies are dosed at 10 milligrams/ kg once weekly for 4 weeks. At the end of the study, tumors are collected in formalin, processed into paraffin, sectioned, and stained with an anti-CD3 antibody (Cell Signaling Technology). Images are acquired at 200× magnification using an Aperio XT ScanScope® and semi-quantitatively analyzed. The percentage of CD3 positive cells to total tumor cells is calculated using Aperio ImageScope software. Results are compared by One Way ANOVA, followed by Holm-Sidak method for multiple comparisons (Sigma Plot 12.5, Systat Software).

In experiments performed as described above, Antibody A1/2 induces $CD3^+$ T cell tumor infiltration in L55 established tumors. The percentage of $CD3^+$ T cells in response to Antibody A1/2 (60%) is higher as compared to BMS20H4.9 (18%) or human IgG (27%) treatments.

We claim:

1. An anti-CD137 (SEQ ID NO: 1) antibody, comprising a heavy chain having the amino acid sequence of SEQ ID NO: 10 and a light chain having the amino acid sequence of SEQ ID NO: 11.

2. An anti-CD137 (SEQ ID NO: 1) antibody, comprising a heavy chain having the amino acid sequence of SEQ ID NO: 10 and a light chain having the amino acid sequence of SEQ ID NO: 13.

3. A mammalian cell expressing an antibody comprising a heavy chain having the amino acid sequence of SEQ ID NO: 10, and a light chain having the amino acid sequence of SEQ ID NO: 11 or the amino acid sequence of SEQ ID NO: 13.

4. A process for producing an antibody comprising cultivating a mammalian cell expressing the antibody and recovering the antibody, wherein the antibody comprises a heavy chain having the amino acid sequence of SEQ ID NO: 10; and a light chain having the amino acid sequence of SEQ ID NO: 11 or the amino acid sequence of SEQ ID NO: 13.

5. The antibody produced by the process of claim 4.

6. A DNA molecule comprising a polynucleotide having the sequence of SEQ ID NO:14 and one of SEQ ID NO:15, SEQ ID NO:16, or SEQ ID NO:17.

7. A mammalian cell comprising the DNA molecule of claim 6.

8. A pharmaceutical composition, comprising the antibody of claim 1 and an acceptable carrier, diluent, or excipient.

9. A pharmaceutical composition, comprising the antibody of claim 2 and an acceptable carrier, diluent, or excipient.

* * * * *

SEQUENCE LISTING

```
<160> NUMBER OF SEQ ID NOS: 21

<210> SEQ ID NO 1
<211> LENGTH: 232
<212> TYPE: PRT
<213> ORGANISM: Homo sapiens

<400> SEQUENCE: 1

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Arg Thr Arg Lys Glu Cys Ser Ser Thr Ser Asn Ala Glu Cys Asp
    50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
    130                 135                 140

Gly Ala Ser Ser Val Thr Pro Pro Ala Pro Ala Arg Glu Pro Gly His
145                 150                 155                 160

Ser Pro Gln Ile Ile Ser Phe Phe Leu Ala Leu Thr Ser Thr Ala Leu
                165                 170                 175

Leu Phe Leu Leu Phe Phe Leu Thr Leu Arg Phe Ser Val Val Lys Arg
            180                 185                 190

Gly Arg Lys Lys Leu Leu Tyr Ile Phe Lys Gln Pro Phe Met Arg Pro
        195                 200                 205
```

Val Gln Thr Thr Gln Glu Glu Asp Gly Cys Ser Cys Arg Phe Pro Glu
    210                 215                 220

Glu Glu Glu Gly Gly Cys Glu Leu
225                 230

<210> SEQ ID NO 2
<211> LENGTH: 13
<212> TYPE: PRT
<213> ORGANISM: Artificial Sequence
<220> FEATURE:
<223> OTHER INFORMATION: Synthetic Construct

<400> SEQUENCE: 2

Lys Ala Ser Gly Gly Thr Phe Ser Ser Tyr Ala Ile Ser
1               5                   10

<210> SEQ ID NO 3
<211> LENGTH: 17
<212> TYPE: PRT
<213> ORGANISM: Artificial Sequence
<220> FEATURE:
<223> OTHER INFORMATION: Synthetic Construct

<400> SEQUENCE: 3

Gly Ile Ile Pro Ile Phe Gly Thr Ala Asn Tyr Ala Gln Lys Phe Gln
1               5                   10                  15

Gly

<210> SEQ ID NO 4
<211> LENGTH: 15
<212> TYPE: PRT
<213> ORGANISM: Artificial Sequence
<220> FEATURE:
<223> OTHER INFORMATION: Synthetic Construct

<400> SEQUENCE: 4

Ala Arg Asp Leu Met Thr Thr Ala Pro Gly Thr Tyr Phe Asp Leu
1               5                   10                  15

<210> SEQ ID NO 5
<211> LENGTH: 11
<212> TYPE: PRT
<213> ORGANISM: Artificial Sequence
<220> FEATURE:
<223> OTHER INFORMATION: Synthetic Construct

<400> SEQUENCE: 5

Gln Ala Ser Gln Asp Ile Gly Asn Ser Leu Gly
1               5                   10

<210> SEQ ID NO 6
<211> LENGTH: 8
<212> TYPE: PRT
<213> ORGANISM: Artificial Sequence
<220> FEATURE:
<223> OTHER INFORMATION: Synthetic Construct

<400> SEQUENCE: 6

Phe Asp Ala Ser Asp Leu Glu Thr
1               5

<210> SEQ ID NO 7
<211> LENGTH: 9
<212> TYPE: PRT
<213> ORGANISM: Artificial Sequence

```
<220> FEATURE:
<223> OTHER INFORMATION: Synthetic Construct

<400> SEQUENCE: 7

Gln Gln Gly Asn Ser Phe Pro Leu Thr
1               5

<210> SEQ ID NO 8
<211> LENGTH: 120
<212> TYPE: PRT
<213> ORGANISM: Artificial Sequence
<220> FEATURE:
<223> OTHER INFORMATION: Synthetic Construct

<400> SEQUENCE: 8

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Leu Met Thr Thr Ala Pro Gly Thr Tyr Phe Asp Leu Trp
            100                 105                 110

Gly Arg Gly Thr Leu Val Thr Val
        115                 120

<210> SEQ ID NO 9
<211> LENGTH: 107
<212> TYPE: PRT
<213> ORGANISM: Artificial Sequence
<220> FEATURE:
<223> OTHER INFORMATION: Sythetic Construct

<400> SEQUENCE: 9

Ala Ile Arg Met Thr Gln Ser Pro Pro Ser Leu Ser Ala Ser Val Gly
1               5                   10                  15

Asp Arg Val Thr Ile Thr Cys Gln Ala Ser Gln Asp Ile Gly Asn Ser
            20                  25                  30

Leu Gly Trp Tyr Gln Gln Lys Pro Gly Lys Ala Pro Lys Leu Val Ile
        35                  40                  45

Phe Asp Ala Ser Asp Leu Glu Thr Gly Val Pro Ser Arg Phe Ser Gly
    50                  55                  60

Ser Gly Ser Gly Thr Asp Phe Ser Leu Thr Ile Ser Ser Leu Gln Pro
65                  70                  75                  80

Glu Asp Phe Ala Thr Tyr Tyr Cys Gln Gln Gly Asn Ser Phe Pro Leu
                85                  90                  95

Thr Phe Gly Gln Gly Thr Arg Leu Glu Ile Lys
            100                 105

<210> SEQ ID NO 10
<211> LENGTH: 452
<212> TYPE: PRT
<213> ORGANISM: Artificial Sequence
<220> FEATURE:
```

<223> OTHER INFORMATION: Synthetic Construct

<400> SEQUENCE: 10

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Leu Met Thr Thr Ala Pro Gly Thr Tyr Phe Asp Leu Trp
            100                 105                 110

Gly Arg Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
210                 215                 220

Cys Asp Lys Thr His Thr Cys Pro Pro Cys Pro Ala Pro Glu Ala Glu
225                 230                 235                 240

Gly Ala Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400
```

```
Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Gly Lys
    450

<210> SEQ ID NO 11
<211> LENGTH: 214
<212> TYPE: PRT
<213> ORGANISM: Artificial Sequence
<220> FEATURE:
<223> OTHER INFORMATION: Synthetic Construct

<400> SEQUENCE: 11

Ala Ile Arg Met Thr Gln Ser Pro Ser Leu Ser Ala Ser Val Gly
1               5                   10                  15

Asp Arg Val Thr Ile Thr Cys Gln Ala Ser Gln Asp Ile Gly Asn Ser
            20                  25                  30

Leu Gly Trp Tyr Gln Gln Lys Pro Gly Lys Ala Pro Lys Leu Val Ile
        35                  40                  45

Phe Asp Ala Ser Asp Leu Glu Thr Gly Val Pro Ser Arg Phe Ser Gly
    50                  55                  60

Ser Gly Ser Gly Thr Asp Phe Ser Leu Thr Ile Ser Ser Leu Gln Pro
65                  70                  75                  80

Glu Asp Phe Ala Thr Tyr Tyr Cys Gln Gln Gly Asn Ser Phe Pro Leu
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 106
<212> TYPE: PRT
<213> ORGANISM: Artificial Sequence
<220> FEATURE:
<223> OTHER INFORMATION: Synthetic Construct

<400> SEQUENCE: 12

Ile Arg Met Thr Gln Ser Pro Ser Leu Ser Ala Ser Val Gly Asp
1               5                   10                  15

Arg Val Thr Ile Thr Cys Gln Ala Ser Gln Asp Ile Gly Asn Ser Leu
            20                  25                  30
```

Gly Trp Tyr Gln Gln Lys Pro Gly Lys Ala Pro Lys Leu Val Ile Phe
            35                  40                  45

Asp Ala Ser Asp Leu Glu Thr Gly Val Pro Ser Arg Phe Ser Gly Ser
        50                  55                  60

Gly Ser Gly Thr Asp Phe Ser Leu Thr Ile Ser Ser Leu Gln Pro Glu
65                  70                  75                  80

Asp Phe Ala Thr Tyr Tyr Cys Gln Gln Gly Asn Ser Phe Pro Leu Thr
                85                  90                  95

Phe Gly Gln Gly Thr Arg Leu Glu Ile Lys
            100                 105

<210> SEQ ID NO 13
<211> LENGTH: 213
<212> TYPE: PRT
<213> ORGANISM: Artificial Sequence
<220> FEATURE:
<223> OTHER INFORMATION: Synthetic Construct

<400> SEQUENCE: 13

Ile Arg Met Thr Gln Ser Pro Ser Leu Ser Ala Ser Val Gly Asp
1               5                   10                  15

Arg Val Thr Ile Thr Cys Gln Ala Ser Gln Asp Ile Gly Asn Ser Leu
            20                  25                  30

Gly Trp Tyr Gln Gln Lys Pro Gly Lys Ala Pro Lys Leu Val Ile Phe
            35                  40                  45

Asp Ala Ser Asp Leu Glu Thr Gly Val Pro Ser Arg Phe Ser Gly Ser
        50                  55                  60

Gly Ser Gly Thr Asp Phe Ser Leu Thr Ile Ser Ser Leu Gln Pro Glu
65                  70                  75                  80

Asp Phe Ala Thr Tyr Tyr Cys Gln Gln Gly Asn Ser Phe Pro Leu Thr
                85                  90                  95

Phe Gly Gln Gly Thr Arg Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 14
<211> LENGTH: 1359
<212> TYPE: DNA
<213> ORGANISM: Artificial Sequence
<220> FEATURE:
<223> OTHER INFORMATION: Synthetic Construct

<400> SEQUENCE: 14
caggtgcagc tggtgcagtc tggggctgag gtgaagaagc ctgggtcctc ggtgaaggtc      60

```
tcctgcaagg cttctggagg caccttcagc agctatgcta tcagctgggt gcgacaggcc    120
cctggacaag ggcttgagtg gatgggaggg atcatccta tctttggtac agcaaactac     180
gcacagaagt tccagggcag agtcacgatt accgcggacg aatccacgag cacagcctac    240
atggagctga gcagcctgag atctgaggac acggccgtgt attactgtgc gagagatctg    300
atgactacgg ccctgggac gtacttcgat ctctggggcc gtggcaccct ggtcactgtc    360
tcctcagcta gcaccaaggg cccatcggtc ttccccctgg cacctcctc caagagcacc     420 tctgggggca gcggccct gggctgcctg gtcaaggact acttccccga accggtgacg      480
gtgtcgtgga actcaggcgc actgaccagc ggcgtgcaca ccttcccggc tgtcctacag    540
tcctcaggac tctactccct cagcagcgtg gtgaccgtgc cctccagcag cttgggcacc    600
cagacctaca tctgcaacgt gaatcacaag cccagcaaca ccaaggtgga caagagagtt    660
gagcccaaat cttgtgacaa aactcacaca tgcccaccgt gcccagcacc tgaagccgag    720 gggcaccgt cagtcttcct cttccccca aaacccaagg acaccctcat gatctcccgg     780 accctgagg tcacatgcgt ggtggtggac gtgagccacg aagaccctga ggtcaagttc     840
aactggtatg tggacggcgt ggaggtgcat aatgccaaga caaagccgcg ggaggagcag    900
tacaacagca cgtaccgtgt ggtcagcgtc ctcaccgtcc tgcaccaaga ctggctgaat    960
ggcaaggagt acaagtgcaa ggtctccaac aaagccctcc catcctccat cgagaaaacc    1020
atctccaaag ccaaagggca gccccgagaa ccacaggtgt acaccctgcc cccatcccgg    1080
gaggagatga ccaagaacca agtcagcctg acctgcctgg tcaaaggctt ctatcccagc    1140
gacatcgccg tggagtggga gagcaatggg cagccggaga caactacaa gaccacgcct    1200 cccgtgctgg actccgacgg ctccttcttc ctctattcca agctcaccgt ggacaagagc    1260
aggtggcagc aggggaacgt cttctcatgc tccgtgatgc atgaggctct gcacaaccac    1320
tacacgcaga gagcctctc cctgtctccg ggcaaatga                            1359
```

<210> SEQ ID NO 15
<211> LENGTH: 645
<212> TYPE: DNA
<213> ORGANISM: Artificial Sequence
<220> FEATURE:
<223> OTHER INFORMATION: Synthetic Construct

<400> SEQUENCE: 15

```
atgaggctgc tgcctctgct ggccctcctg ccctgtgggg cccagaccc agccagagcc     60 gccatccgga tgacccagtc tccaccctcc ctgtctgcat ctgtaggaga cagagtcacc    120
atcacttgcc aggcgagtca ggacattggc aactctttag gttggtatca gcagaaacca    180
gggaaagccc ctaaactcgt gatcttcgat gcatcagatc tggaaacagg gtcccatca    240 aggttcagtg gcagtggatc tggcacagat ttcagtctca ccatcagcag cctgcagcct    300
gaggattttg caacttacta ttgtcaacag ggtaacagtt tcccgctcac cttcggccaa    360
gggacacgac tggagattaa acgaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                   645
```

<210> SEQ ID NO 16

<211> LENGTH: 702
<212> TYPE: DNA
<213> ORGANISM: Artificial Sequence
<220> FEATURE:
<223> OTHER INFORMATION: Synthetic Construct

<400> SEQUENCE: 16

```
atggagacag acacactcct gctatgggta ctgctgctct gggttccagg ctccaccggc    60
atccggatga cccagtctcc accctccctg tctgcatctg taggagacag agtcaccatc   120
acttgccagg cgagtcagga cattggcaac tctttaggtt ggtatcagca gaaaccaggg   180
aaagccccta aactcgtgat cttcgatgca tcagatctgg aaacaggggt cccatcaagg   240
ttcagtggca gtggatctgg cacagatttc agtctcacca tcagcagcct gcagcctgag   300
gattttgcaa cttactattg tcaacagggt aacagtttcc cgctcacctt cggccaaggg   360
acacgactgg agattaaacg aactgtggcc gcaccatctg tcttcatctt cccgccatct   420
gatgagcagt tgaaatctgg aactgcctct gttgtgtgcc tgctgaataa cttctatccc   480
agagaggcca agtacagtg aaggtggat aacgccctcc aatcgggtaa ctcccaggag    540
agtgtcacag agcaggacag caaggacagc acctacagcc tcagcagcac cctgacgctg   600
agcaaagcag actacgagaa acacaaagtc tacgcctgcg aagtcacccca tcagggcctg   660
agctcgcccg tcacaaagag cttcaacagg ggagagtgtt ag                       702
```

<210> SEQ ID NO 17
<211> LENGTH: 705
<212> TYPE: DNA
<213> ORGANISM: Artificial Sequence
<220> FEATURE:
<223> OTHER INFORMATION: Synthetic Construct

<400> SEQUENCE: 17

```
atggagacag acacactcct gctatgggta ctgctgctct gggttccagg ctccaccggc    60
gccatccgga tgacccagtc tccaccctcc ctgtctgcat ctgtaggaga cagagtcacc   120
atcacttgcc aggcgagtca ggacattggc aactctttag gttggtatca gcagaaacca   180
gggaaagccc ctaaactcgt gatcttcgat gcatcagatc tggaaacagg gtcccatca   240
aggttcagtg gcagtggatc tggcacagat ttcagtctca ccatcagcag cctgcagcct   300
gaggattttg caacttacta ttgtcaacag ggtaacagtt tcccgctcac cttcggccaa   360
gggacacgac tggagattaa acgaactgtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgccc tccaatcggg taactcccag   540
gagagtgtca cagagcagga cagcaaggac agcacctaca gcctcagcag cacccctgacg   600
ctgagcaaag cagactacga gaaacacaaa gtctacgcct gcgaagtcac ccatcagggc   660
ctgagctcgc ccgtcacaaa gagcttcaac aggggagagt gttag                    705
```

<210> SEQ ID NO 18
<211> LENGTH: 448
<212> TYPE: PRT
<213> ORGANISM: Artificial Sequence
<220> FEATURE:
<223> OTHER INFORMATION: Synthetic

<400> SEQUENCE: 18

```
Gln Val Gln Leu Gln Gln Trp Gly Ala Gly Leu Leu Lys Pro Ser Glu
  1               5                  10                  15
```

-continued

```
Thr Leu Ser Leu Thr Cys Ala Val Tyr Gly Gly Ser Phe Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
```

```
                     435                 440                 445

<210> SEQ ID NO 19
<211> LENGTH: 216
<212> TYPE: PRT
<213> ORGANISM: Artificial Sequence
<220> FEATURE:
<223> OTHER INFORMATION: synthetic

<400> SEQUENCE: 19

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 20
<211> LENGTH: 442
<212> TYPE: PRT
<213> ORGANISM: Artificial Sequence
<220> FEATURE:
<223> OTHER INFORMATION: synthetic

<400> SEQUENCE: 20

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80
```

```
Leu Gln Trp Ser Ser Leu Lys Ala Ser Asp Thr Ala Met Tyr Tyr Cys
                 85                  90                  95

Ala Arg Gly Tyr Gly Ile Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
        195                 200                 205

Lys Val Asp Lys Thr Val Glu Arg Lys Cys Cys Val Glu Cys Pro Pro
    210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Phe Arg Val Val Ser Val Leu Thr Val Val
    290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 21
<211> LENGTH: 214
<212> TYPE: PRT
<213> ORGANISM: Artificial Sequence
<220> FEATURE:
<223> OTHER INFORMATION: synthetic

<400> SEQUENCE: 21
```

-continued

```
Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
            35                  40                  45

Gln Asp Lys Asn Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
        210
```